United States Patent
Zhang et al.

(10) Patent No.: US 7,511,048 B2
(45) Date of Patent: Mar. 31, 2009

(54) PYRIMIDOTHIENOINDAZOLES

(75) Inventors: Chengzhi Zhang, Orange, CT (US); Roger Smith, Madison, CT (US); Gan Wang, Wallingford, CT (US); Sharad Verma, New Haven, CT (US); Qingming Zhu, Malden, MA (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 11/666,362

(22) PCT Filed: Oct. 26, 2005

(86) PCT No.: PCT/US2005/039901

§ 371 (c)(1),
(2), (4) Date: Apr. 25, 2007

(87) PCT Pub. No.: WO2006/055268

PCT Pub. Date: May 26, 2006

(65) Prior Publication Data

US 2007/0299066 A1 Dec. 27, 2007

Related U.S. Application Data

(60) Provisional application No. 60/622,640, filed on Oct. 27, 2004.

(51) Int. Cl.
*C07D 239/00* (2006.01)
*C07D 471/00* (2006.01)
*C07D 471/04* (2006.01)
*C07D 471/22* (2006.01)
*C07D 487/00* (2006.01)
*C07D 487/04* (2006.01)
*C07D 491/00* (2006.01)

(52) U.S. Cl. ........................ 514/257; 544/247
(58) Field of Classification Search .................. 544/247; 514/257
See application file for complete search history.

(56) References Cited

FOREIGN PATENT DOCUMENTS

| WO | 9519970 | 6/1995 |
| WO | 9713760 | 4/1997 |
| WO | WO2006/023843 | * 2/2006 |
| WO | 2006023843 | 3/2006 |

OTHER PUBLICATIONS

West, Anthony R., Solid State Chemistry and Its Applications, Wiley, New York, 1988, 358.*
Pillon, et al., In vivo bioluminescence imaging to evaluate estrogenic activities of endocrine disrupters, Analytical Biochemistry, (May 15, 2005) vol. 340, No. 2, pp. 295-302.*
Showalter, et al., "Tyrosine Kinase Inhibitors. 16.6,5,6-Tricyclic Benzothieno [3,2-d]pyrimidines and Pyrimido[5,4-b]- and -[4,5-b]indoles as Potent Inhibitors of the Epidermal Growth Factor Receptor Tyrosine Kinase", J. Med. Chem., 42: 5464-5474 (1999).

* cited by examiner

*Primary Examiner*—James O Wilson
*Assistant Examiner*—Erich A Leeser
(74) *Attorney, Agent, or Firm*—Edwards Angell Palmer & Dodge LLP; Barry Kramer; Ralph Loren

(57) ABSTRACT

The invention relates to novel pyrimidothienoindazoles of formula (I)

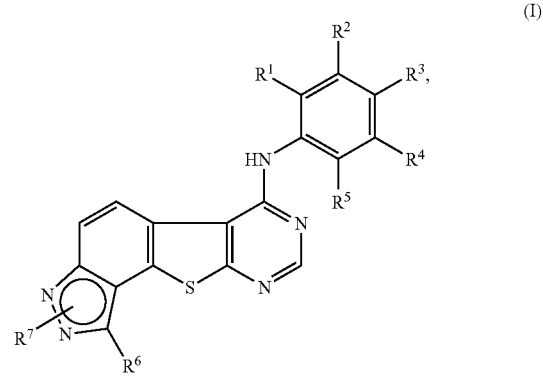

processes for their preparation and their use for preparing medicaments for the treatment or prophylaxis of disorders, especially of hyperproliferative disorders.

10 Claims, No Drawings

PYRIMIDOTHIENOINDAZOLES

This application claims benefit of U.S. Provisional Application Ser. No. 60/622,640; filed on Oct. 27, 2004, the content of which is incorporated herein by reference in its entirety.

This invention relates to novel pyrimidothienoindazoles, processes for their preparation and their use for preparing medicaments for the treatment or prophylaxis of disorders, especially of hyperproliferative disorders.

Epidermal growth factor receptors (EGFRs) comprise a family consisting of four known tyrosine kinase receptors, HER1 (EGFR, ErbB1), HER2 (neu, ErbB2), HER3 (ErbB3) and HER4 (ErbB4). These receptors are activated by a number of ligands including EGF, TGFα, epiregulin, amphiregulin and heregulins (neuregulins). The HER family receptors generate cell signaling cascades that transduce extracellular stimulation into intracellular events that control various cellular functions including proliferation, differentiation and apoptosis. These receptors are elevated in a large number of solid tumors and this increase has been associated with the disruption of normal cellular control resulting in more aggressive tumors and a poor disease prognosis. Inhibitors of epidermal growth factor receptors have resulted in stabilization or regression of tumor growth in a broad range of tumor types (Holbro, T., Civenni, G., and Hynes, N. Exp Cell Res. 284: 99-110, 2003). It is believed that the compounds in this invention provide their anti-proliferative effect through the inhibition of the tyrosine kinase activities of epidermal growth factor receptors (in particular ErbB1 and ErbB2).

U.S. Pat. No. 5,679,683 (Pfizer) and WO 97/13760 (Glaxo Welcome) describe tricyclic compounds capable of inhibiting tyrosine kinases of the epidermal growth factor receptor family.

U.S. Pat. No. 6,482,948 (Nippon Soda), U.S. Pat. No. 6,130,223, U.S. Pat. No. 6,495,557, WO 00/78767, WO 01/019369, WO 01/021620, US 2003/153585, U.S. 2003/022906, U.S. 2004/058940, U.S. 2004/077664 and WO 02/072100 (Merck GmbH) disclose tricyclic compounds as PDE inhibitors.

WO 03/057149 (Bayer) describes heteropyrimidines and hetero-4-pyrimidones for the treatment of $PDE7_B$-mediated diseases.

The present invention relates to a compound of formula (I)

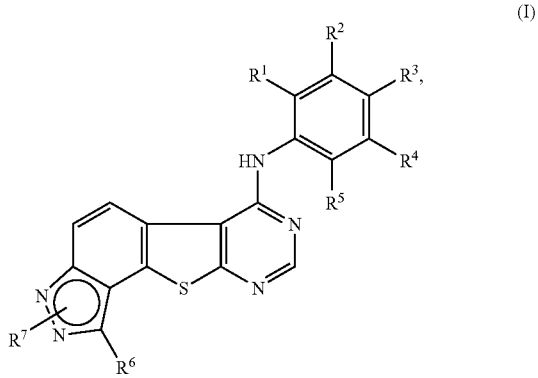

(I)

wherein
$R^1$ is selected from the group consisting of hydrogen, methyl, ethyl, and halo;
$R^2$ is selected from the group consisting of hydrogen, methyl, ethyl, and halo;
$R^3$ is selected from the group consisting of hydrogen, alkyl, halo, hydroxy, alkoxy, trifluoromethoxy, benzyloxy, halogenated benzyloxy, alkylated benzyloxy, pyridoxy, alkylated pyridoxy, halogenated pyridoxy, pyridylmethoxy, halogenated pyridylmethoxy, and N-morpholinyl, or
$R^2$ and $R^3$, together with the carbon atoms to which they are attached, form an pyrazole ring, wherein said pyrazole ring can optionally be substituted with 0, 1 or 2 substituents independently selected from the group consisting of alkyl, benzyl, halogenated benzyl, pyridylmethoxy, and halogenated pyridylmethoxy;
$R^4$ is selected from the group consisting of hydrogen, alkyl, cyano, and halo;
$R^5$ is selected from the group consisting of hydrogen, alkyl, and halo;
$R^6$ is selected from the group consisting of hydrogen, and alkyl;
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, hydroxy, alkoxy, alkylsulfonyloxy, and amino, or
$R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or
$R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$,
wherein $R^{7-2}$ is oxo, or
wherein $R^{7-2}$ is alkylamino, wherein said alkylamino can optionally be substituted with 0, 1 or 2 substituents independently selected from the group consisting of oxo, hydroxy, alkoxy, amino, and alkylamino;
or its salt, solvate or solvate of the salt.

Depending on their structure, the compounds according to the invention can exist in stereoisomeric forms (enantiomers, diastereomers). The invention therefore relates to the enantiomers or diastereomers and to their respective mixtures. Such mixtures of enantiomers and/or diastereomers can be separated into stereoisomerically unitary constituents in a known manner.

The invention also relates to tautomers of the compounds, depending on the structure of the compounds.

Salts for the purposes of the invention are preferably pharmacologically acceptable salts of the compounds according to the invention.

Pharmacologically acceptable salts of the compounds (I) include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid.

Pharmacologically acceptable salts of the compounds (I) also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietylamine, arginine, lysine, ethylenediamine and methylpiperidine.

Solvates for the purposes of the invention are those forms of the compounds that coordinate with solvent molecules to form a complex in the solid or liquid state. Hydrates are a specific form of solvates, where the coordination is with water.

For the purposes of the present invention, the substituents have the following meanings, unless otherwise specified:

Alkyl per se and "alk" and "alkyl" in other radicals represent a linear or branched alkyl radical having 1 to 6, or, in another embodiment, 1 to 4, or in yet another embodiment 1 to 3 carbon atoms, representing illustratively methyl, ethyl, n-propyl, isopropyl, tert-butyl, n-pentyl and n-hexyl.

Alkenyl represents a linear or branched alkyl radical having one or more double bonds and 2 to 6, or, in another embodiment, 2 to 4, or in yet another embodiment 2 to 3 carbon atoms, representing illustratively allyl.

Alkoxy represents a straight-chain or branched hydrocarbon radical having 1 to 6, or, in another embodiment, 1 to 4, or in yet another embodiment 1 to 3 carbon atoms and bound via an oxygen atom. Non-limiting examples include methoxy, ethoxy, propoxy, isopropoxy, butoxy, isobutoxy, pentoxy, isopentoxy, hexoxy, isohexoxy. The terms "alkoxy" and "alkyloxy" can be used synonymously.

Alkylamino represents an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Alkenylamino represents an amino radical having one or two (independently selected) alkenyl substituents, illustratively representing allylamino.

Alkylsulfonyloxy represents *—OS(O)$_2$alkyl.

Alkylsulfonyl represents *—S(O)$_2$alkyl

Alkoxycarbonyl represents an alkoxy radical bound via a carbonyl group, e.g. methoxycarbonyl, ethoxycarbonyl, n-propoxycarbonyl, isopropoxycarbonyl, tert-butoxycarbonyl, n-pentoxycarbonyl and n-hexoxycarbonyl.

Aryl represents a mono- to tricyclic carbocyclic radical, which is aromatic at least in one ring and bound via an oxygen atom, having generally 6 to 14 carbon atoms, illustratively representing phenyl, naphthyl and phenanthrenyl.

Heteroaryl represents an mono- or bicyclic radical having generally 5 to 10 and preferably 5 or 6 ring atoms and up to 5 and preferably up to 4 hetero atoms selected from the group consisting of nitrogen, oxygen and sulfur, which is aromatic at least in one ring. It can be attached via a ring carbon atom or a ring nitrogen atom. If it represents a bicycle, wherein one ring is aromatic and the other one is not, it can be attached at both rings. Illustrative examples are thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heterocyclyl represents a mono- or polycyclic, preferably mono- or bicyclic, nonaromatic heterocyclic radical having 4 to 10, or, in another embodiment, 5 to 8, or in yet another embodiment 5 or 6 ring atoms and up to 3, or, in another embodiment, 1 or 2 hetero atoms and/or hetero groups selected from the group consisting of nitrogen, oxygen and sulfur, SO and SO$_2$. It can be attached via a ring carbon atom or a ring nitrogen atom. Illustrative examples are tetrahydrofuran-2-yl, pyrrolidin-2-yl, pyrrolidin-3-yl, pyrrolinyl, piperidinyl, morpholinyl, perhydroazepinyl.

Pyridylmethoxy represents a pyridyl substituent attached to the carbon atom of a methoxy group, e.g. 2-pyridylmethoxy.

Halogen represents fluorine, chlorine, bromine and iodine.

An asterisk (*) symbol next to a bond denotes the point of attachment in the molecule.

The depiction of $R^7$ in formula (I) with a bond directed into the aromatic pyrazole ring means that one $R^7$ can be attached to one of the two nitrogen atoms in said aromatic pyrazole ring, i.e. either to the nitrogen atom next to the carbon atom substituted with $R^6$ or to the other one.

When the conjunction "or" connects two part sentences of a claim defining alternative definitions for a substituent which can be present in a number larger than one, said "or" may also be interpreted as an "and".

If radicals in the compounds according to the invention are substituted, the radicals, unless otherwise specified, can be substituted by one or more identical or different substituents. A substitution with up to three identical or different substituents is preferred. Very particular preference is given to substitution with one substituent. When a nitrogen-containing molecule is further substituted, the substitution preferably does not take place on the nitrogen atom, if such substitution leads to quaternization of said nitrogen atom, e.g. in the case of alkylation.

Except for intermediates, chemically unstable compounds are less preferred in the context of the present invention. The expression chemically unstable here is meant to include conditions to which a compound is exposed when administered to a patient in need thereof, such as acidic or basic conditions of the gastrointestinal tract. For example, a chemically unstable compound would be one where two nitrogen or oxygen substituents are bonded to a single aliphatic carbon atom. Another example of a chemically unstable compound would be one where an alkoxy group is bonded to the unsaturated carbon of an alkene to form an enol ether. Furthermore, an aliphatic carbon atom attached to oxygen may not also bear a chloro, bromo or iodo substituent, and when any alkyl group is attached to O, S, or N, and bears a hydroxyl substituent, then the hydroxyl substituent is separated by at least two carbon atoms from the O, S, or N to which the alkyl group is attached.

In another embodiment, the present invention provides compounds of the formula (I), wherein
$R^1$ is hydrogen;
$R^2$ is hydrogen;
$R^3$ is selected from the group consisting of hydrogen, halo, hydroxy, methoxy, ethoxy, n-propyloxy, i-propyloxy, trifluoromethoxy, benzyloxy, halogenated benzyloxy, pyridoxy, methylated pyridoxy, ethylated pyridoxy, halogenated pyridoxy, pyridylmethoxy, halogenated pyridylmethoxy, and N-morpholinyl, or
$R^2$ and $R^3$, together with the carbon atoms to which they are attached, form an pyrazole ring, wherein said pyrazole ring can optionally be substituted with 0 or 1 substituents benzyl;
$R^4$ is selected from the group consisting of hydrogen, methyl, ethyl, n-propyl, i-propyl, cyano, and halo;
$R^5$ is hydrogen;
$R^6$ is hydrogen;
$R^7$ is selected from the group consisting of hydrogen, methyl, ethyl, n-propyl, i-propyl, n-butyl, i-butyl, t-butyl, and amino, or
$R^7$ is alkyl selected from the group consisting of methyl, ethyl, and n-propyl, wherein said alkyl is substituted with 1 or 2 independently selected substituents $R^{7-1}$,
wherein $R^{7-1}$ is selected from the group consisting of halo, hydroxy, methoxy, ethoxy, n-propyloxy, i-propyloxy, methylsulfonyloxy, amino, or
$R^{7-1}$ is alkylamino, wherein said alkylamino can optionally be substituted with 0, 1 or 2 substituents independently selected from the group consisting of hydroxy, methoxy, ethoxy, n-propyloxy, i-propyloxy, amino, methylamino, ethylamino, dimethylamino, diethylamino, methylethylamino, methylsulfonyl, N-pyrrolidinyl, and N-morpholinyl, or
$R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0 or 1 substituents independently selected from the group consisting of methyl, ethyl, n-propyl, i-propyl, halo, hydroxy, methoxy, ethoxy, n-propyloxy, i-propyloxy, amino, methylamino, ethylamino, dimethylamino, diethylamino, methylethylamino, hydroxymethyl, hydroxyethyl, methoxymethyl, methoxyethyl, carboxyl, methoxycarbonyl, ethoxycarbonyl, n-propyloxycarbonyl, i-propyloxycarbonyl, n-butyloxycarbonyl, i-butyloxycarbonyl, t-butyloxycarbonyl, N-pyrrolidinyl, N-piperidinyl, N-piperazinyl, pyrazinyl, benzyl, and pyridylmethyl;
or its salt, solvate or solvate of the salt.

In another embodiment, the present invention provides compounds of the formula (I), wherein $R^1$, $R^2$, and $R^5$ are hydrogen, $R^3$ is 2-pyridylmethoxy and $R^4$ is chloro.

In another embodiment, the present invention provides compounds of the formula (I), wherein $R^1$, $R^2$, and $R^5$ are hydrogen, $R^3$ is fluoro and $R^4$ is chloro.

In another embodiment, the present invention provides compounds of the formula (I), wherein $R^1$, $R^2$, $R^4$, and $R^5$ are hydrogen, and $R^3$ is 3-fluorobenzyloxy.

In another embodiment, the present invention provides a process for preparing the compounds of the formula (I), wherein a compound of formula (II)

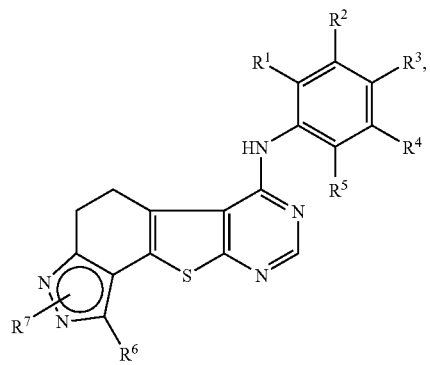

(II)

wherein $R^1$ to $R^7$ have the meaning indicated above,
is oxidized with a oxidising agent or oxidant, such as DDQ.

In another embodiment, the present invention provides a process for preparing the compounds of the formula (Ic),

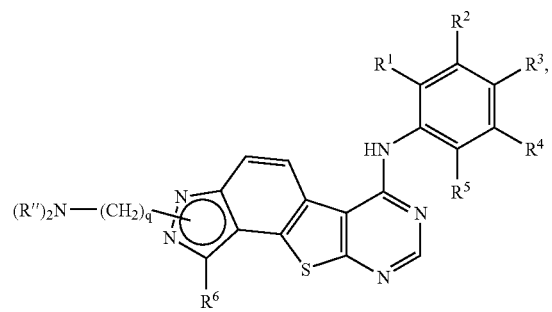

(Ic)

wherein $R^1$ to $R^6$ have the meaning indicated above, q is 2, 3 or 4, and R" is hydrogen, alkyl, or may be joined to form a heterocyclic ring,
wherein a compound of formula

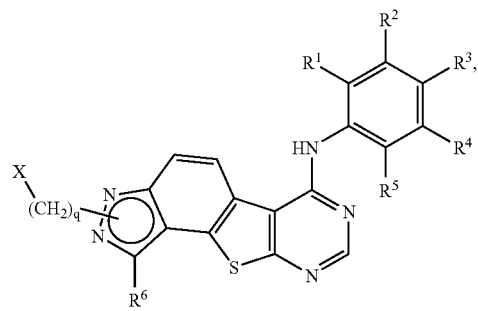

(Ib)

wherein $R^1$ to $R^6$ have the meaning indicated above, q is 2, 3 or 4, and X is halo or MsO,
is reacted with a compound of formula (R")$_2$NH wherein R" is hydrogen, alkyl, or may be joined to form a heterocyclic ring.

Accordingly, a compound of formula (II), as well as a compound of formula (Ib) are valuable precursors for making a compound of the present invention, and are as such also part of the present invention.

The preparation of the compounds according to the invention can be illustrated by means of the following synthetic schemes. In these schemes, unless specifically designated otherwise, $R^1$-$R^7$ are as defined for formula (I) above.

In general, compounds of formula (I) can be prepared from the route outlined in Reaction Scheme 1. In this scheme, a mono-protected cyclohexane-1-4-dione of formula (1) is allowed to react with a cyanoacetic acid ester of formula (2) in the presence of sulfur and a base, to form the bicyclic aminothiophene carboxylic acid ester of formula (3). Reaction of this compound with either formamidine or formamide gives the tricyclic thiopyrimidone of formula (4). Reaction of the formula (4) compound with a halogenating agent such as $POCl_3$ gives the chloro derivative of formula (5). The tricyclic compound of formula (5) is allowed to react with a substituted aniline of formula (6) in the presence of a base and a polar solvent such as ethanol to give the intermediate of formula (7). Hydrolysis of (7) under aqueous acidic conditions provides the ketone of formula (8). Reaction of (8) with a N,N-dimethylamide dimethyl acetal, such as DMF dimethylacetal, gives an enaminone intermediate of formula (9). This intermediate is then condensed with a hydrazine of general formula HO—$(CH_2)_q$—$NHNH_2$ (wherein q=2, 3, or 4), to give the compound of formula (10). Oxidation of (10) using reagent such as DDQ affords the compound of formula (Ia) [(formula (I), where $R^7$ is a hydroxy-substituted alkyl group]. This formula (Ia) compound can be converted to the corresponding formula (Ib) compound [(I), where $R^7$ is haloalkyl or alkysulfonyloxyalkyl], by reaction of (Ia) with a halogenating agent such as $SOBr_2$ or with an alkanesulfonyl chloride such as methanesulfonyl chloride. The compound of formula (Ib) may be converted to the compound of formula (Ic) [(I), where $R^7$ is alkyl substituted by $R^{7-1}$, where $R^{7-1}$ is an amino, alkylamino or heterocycle] by allowing it to react with a secondary or primary amine, such as diethylamine or with an optionally substituted nitrogen heterocycle, such as a pyrrolidine, a piperidine, or a morpholine, provided the N-atom of the heterocycle remains unsubstituted.

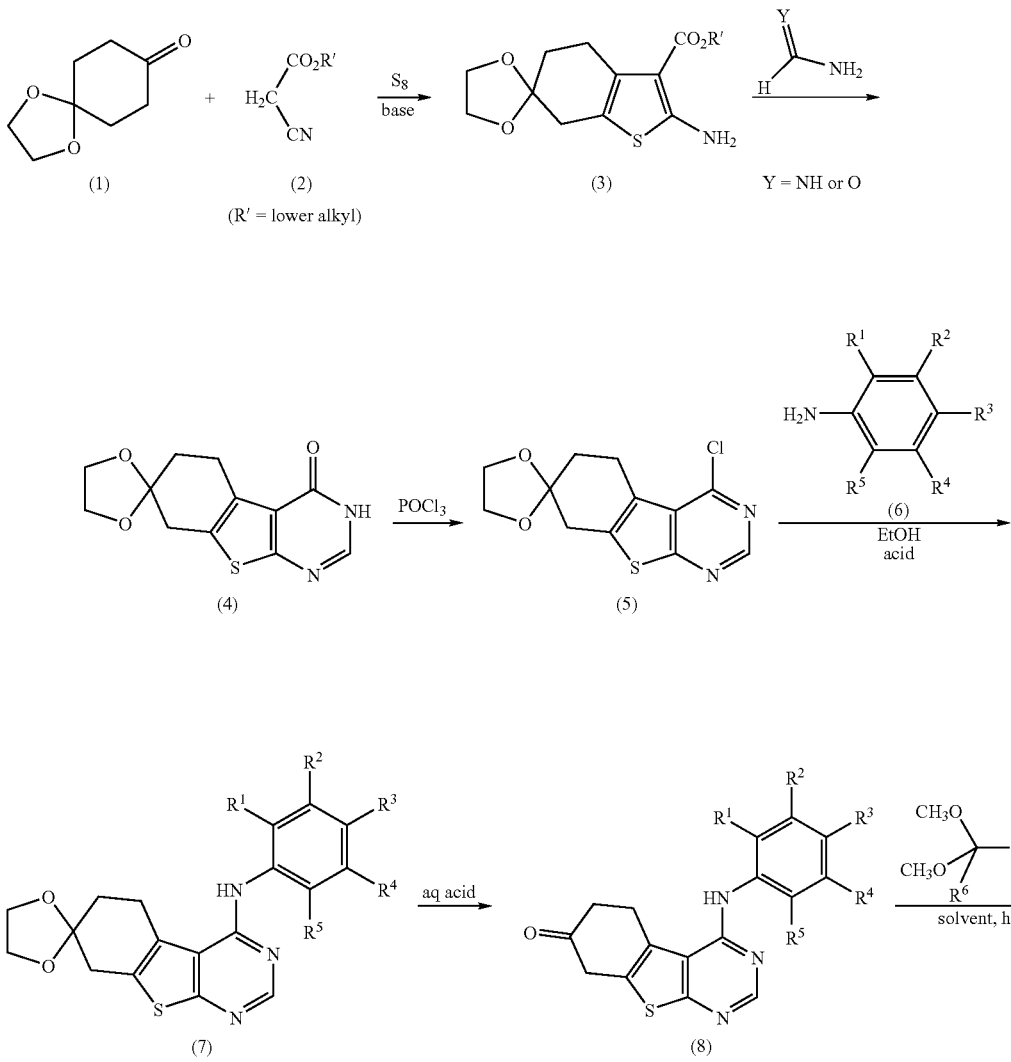

-continued
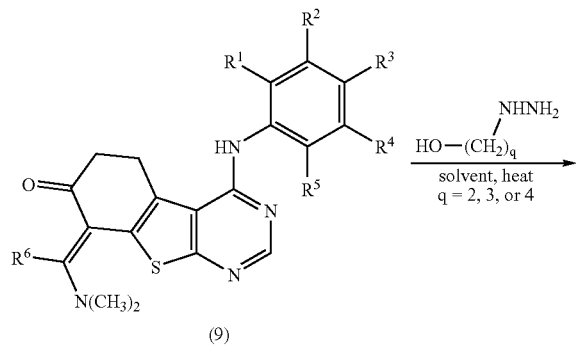
(9)
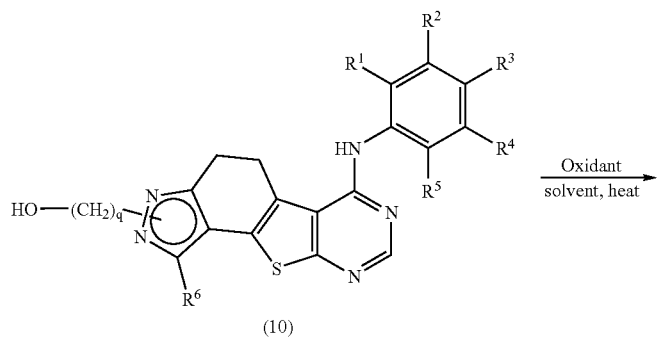
(10)
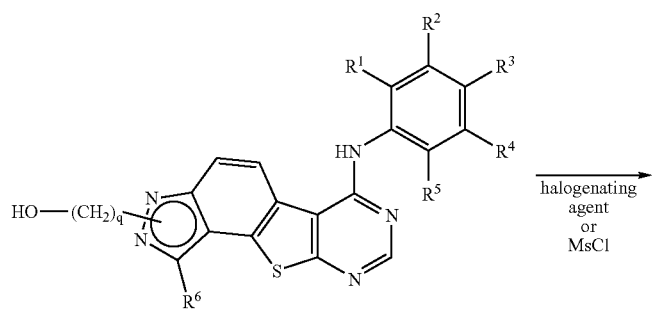
(Ia): [(I), where $R^7$ is hydroxy($C_2$-$C_4$)alkyl-]
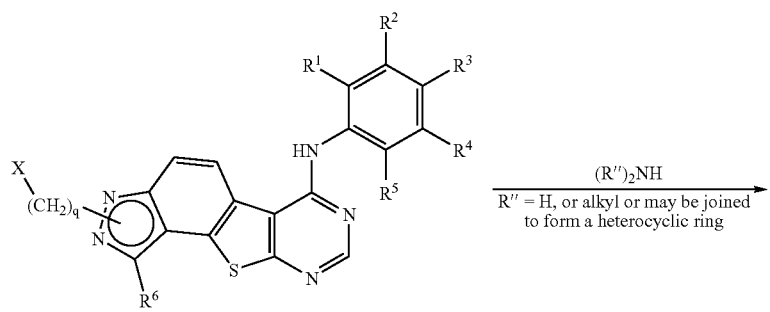
X = halo or MsO
(Ib): [(I), where $R^7$ is halo($C_2$-$C_4$)alkyl-] or MsO—($C_2$-$C_4$)alkyl-

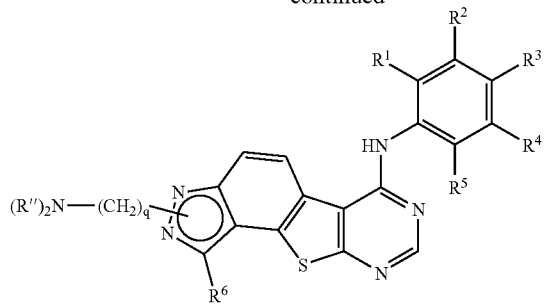

(Ic): [(I)] where $R^7 = (R'')_2$N-alkyl-

Compound (10) described in Reaction Scheme 1 may provide regioisomeric mixtures in which the location of the $R^7$ group may be on either nitrogen atom of the fused pyrazole ring. These regioisomers may be separated, as desired, by standard chromatographic methods. However, Reaction Schemes 2 and 3 illustrate general methods to prepare the individual regioisomers of compound (10), and their subsequent use to prepare compounds of formula (I).

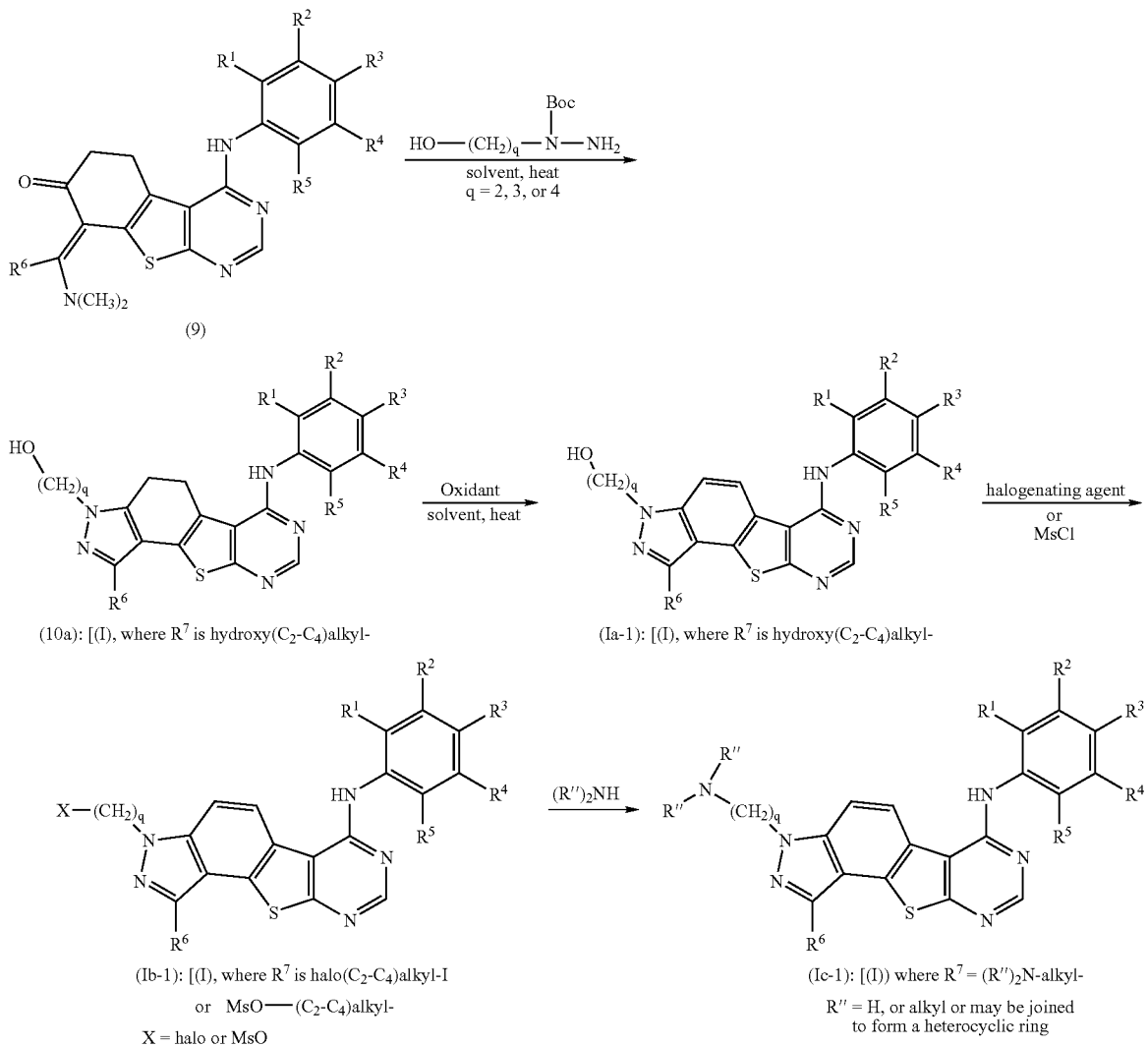

In Reaction Scheme 2, the pyrazole ring-forming reaction is carried out using the enaminone of formula (9) and a 1-hydroxyalkylhyrazine carboxylate of general formula HO—(CH$_2$)$_q$—N(NH$_2$)—CO$_2$alkyl, where q is 2, 3 or 4. By this method, the regioisomer of formula (10a) is prepared. Reaction of (10a) with DDQ, followed by treatment with a halogenating or sulfonylating agent in a manner analogous to that described in Reaction Scheme 1, provides the regioisomer of formula (Ib-1). Reaction of (Ib-1) with (R")$_2$NH gives the regioisomer of formula (Ic-1).

alkylsulfonylation, and (Ib-2) is then converted to (Ic-2) by reaction with an amine of general formula (R")$_2$NH.

By using these general methods and adjusting the starting materials and conditions as needed, one skilled in the art can prepare the compounds of the invention.

Additional compounds of formula (I) can be prepared from other formula (I) compounds by elaboration of functional groups present. Such elaboration includes, but is not limited to, hydrolysis, reduction, oxidation, alkylation, acylation,

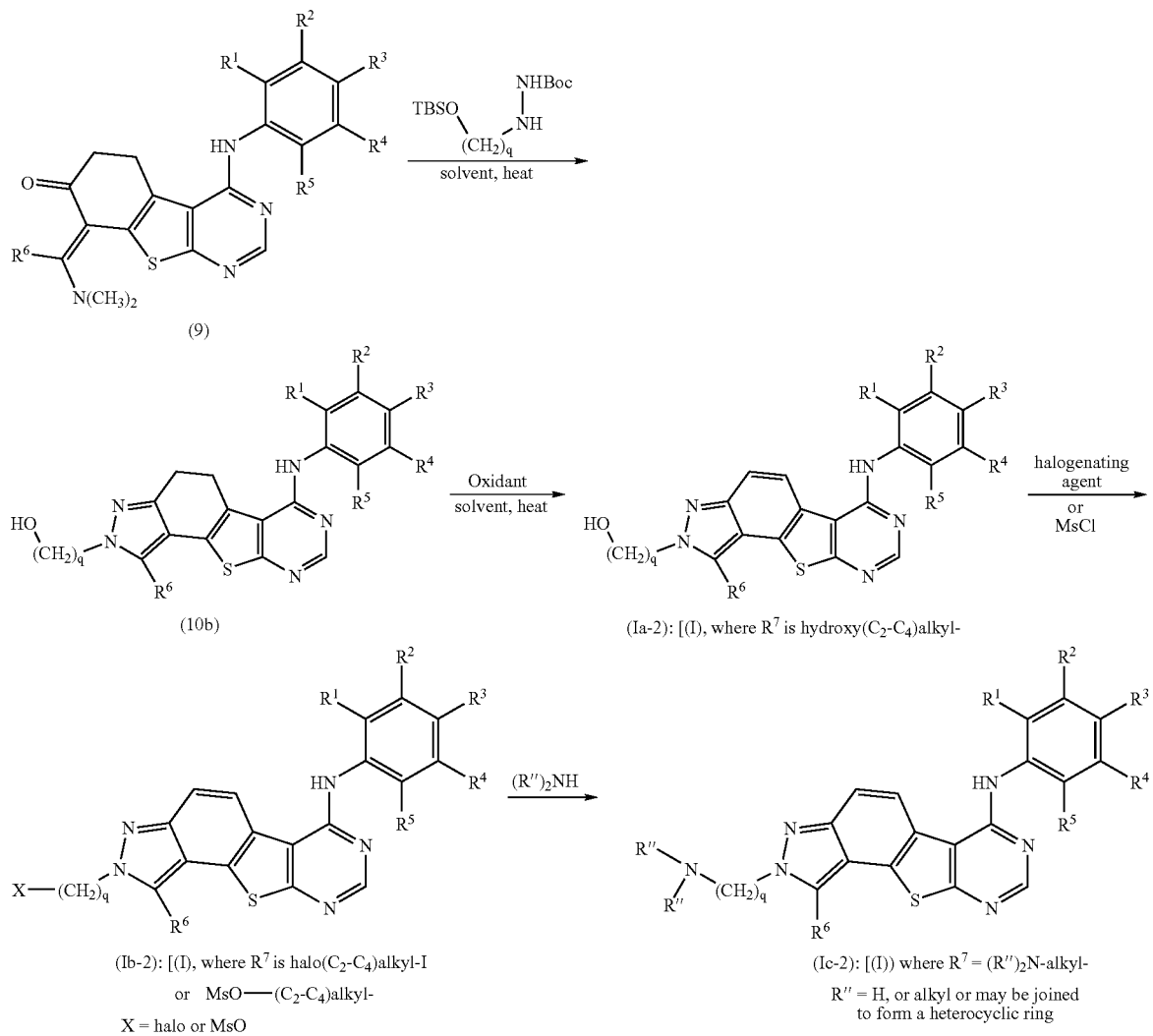

Reaction Scheme 3

In Reaction Scheme 3 is illustrated the preparation of the compounds of formulae 10b, Ia-2, Ib-2 and Ic-2, examples of the other formula (I) regioisomer. The pyrazole ring-is formed in the first step of this scheme: a doubly protected hydrazine, namely 2-tert-butyldimethylsilyloxy-1-tert-butyloxycarbonyl-alkylhydrazine, is allowed to react with the compound of formula (9) to provide the compound of formula (10b). The preparation of compounds of formula (Ia-2) and (Ib-2) is then carried out in a manner identical to that described for formulae (Ia-1) and (Ib-1): The hydroxyalkylpyrazole (Ia-2) is converted to (Ib-2) by halogenation or esterification, amidation and dehydration reactives. Such transformations may in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

The compounds according to the invention exhibit an unforeseeable, useful pharmacological and pharmacokinetic activity spectrum. They are therefore suitable for use as medicaments for the treatment and/or prophylaxis of disorders in humans and animals.

The compounds according to the invention are because of their pharmacological properties useful alone or in combination with other active components for treating and/or preventing hyperproliferative disorders, especially cancer.

In another embodiment, the present invention provides a medicament containing at least one compound according to the invention. In another embodiment, the present invention provides a medicament containing at least one compound according to the invention together with one or more pharmacologically safe excipient or carrier substances, and also their use for the abovementioned purposes.

The active compound can act systemically and/or locally. For this purpose it can be administered in a suitable manner, such as for example by oral, parenteral, pulmonary, nasal, sublingual, lingual, buccal, rectal, dermal, transdermal, ophtalmic or otic administration or in the form of an implant or stent. The active compound can be administered in forms suitable for these modes of administration.

Suitable forms of oral administration are those according to the prior art which function by releasing the active compound rapidly and/or in a modified or controlled manner and which contain the active compound in a crystalline and/or amorphous and/or dissolved form, such as for example tablets (which are uncoated or coated, for example with enteric coatings or coatings which dissolve after a delay in time or insoluble coatings which control the release of the active compound), tablets or films/wafers which disintegrate rapidly in the oral cavity or films/lyophilisates, capsules (e.g. hard or soft gelatin capsules), dragées, pellets, powders, emulsions, suspensions and solutions.

Parenteral administration can be carried out by avoiding an absorption step (e.g. by intravenous, intraarterial, intracardial, intraspinal or intralumbar administration) or by including absorption (e.g. by intramuscular, subcutaneous, intracutaneous or intrapelitoneal administration). Suitable parenteral administration forms are for example injection and infusion formulations in the form of solutions, suspensions, emulsions, lyophilisates and sterile powders.

Suitable forms of administration for the other modes of administration are for example inhalation devices (such as for example powder inhalers, nebulizers), nasal drops, solutions and sprays; tablets or films/wafers for lingual, sublingual or buccal administration or capsules, suppositories, ear and eye preparations, vaginal capsules, aqueous suspensions (lotions or shaking mixtures), lipophilic suspensions, ointments, creams, transdermal therapeutic systems, milky lotions, pastes, foams, dusting powders, implants or stents.

The active compounds can be converted into the abovementioned forms of administration in a manner known to the skilled man and in accordance with the prior art using inert, non-toxic, pharmaceutically suitable auxiliaries. The latter include for example excipients (e.g. microcrystalline cellulose, lactose, mannitol, etc.), solvents (e.g. liquid polyethylene glycols), emulsifiers and dispersants or wetting agents (e.g. sodium dodecyl sulphate, polyoxysorbitan oleate etc.), binders (e.g. polyvinyl pyrrolidone), synthetic and/or natural polymers (e.g. albumin), stabilizers (e.g. antioxidants, such as, for example, ascorbic acid), dyes (e.g. inorganic pigments such as iron oxides) or taste- and/or odour-corrective agents.

In general it has proven advantageous for parenteral administration to administer daily quantities of approximately from 0.001 to 300 mg/kg body weight, and preferably approximately from 0.10 to 150 mg/kg body weight in order to obtain effective results.

It may however be necessary to deviate from the abovementioned quantities, depending on the body weight, mode of administration, the individual patient response to the active compound, the type of preparation and the time or interval of administration.

The percentages in the tests and examples which follows are, unless otherwise stated, by weight; parts are by weight. Solvent ratios, dilution ratios and concentrations reported for liquid/liquid solutions are each based on the volume.

A. EXAMPLES

Abbreviations and Acronyms

When the following abbreviations are used throughout the disclosure, they have the following meaning:
aq aqueous
Boc tert-butoxycarbonyl
$CDCl_3$-d chloroform-d
$CD_2Cl_2$-$d_4$ methylene chloride-d
$CD_3OD$-$d_4$ methanol-$d_4$
Celite® brand of diatomaceous earth, Celite Corporation
d doublet
dd double doublet
DDQ 2,3-dichloro-5,6-dicyanobenzoquinone
DMF N,N-dimethyl formamide
DMSO-$d_6$ dimethylsulfoxide-$d_6$
EtOAc ethyl acetate
EtOH ethanol
equiv equivalent(s)
h hour(s)
$^1$H NMR proton nuclear magnetic resonance
HPLC high performance liquid chromatography
LCMS liquid chromatography/mass spectroscopy
min minute(s)
Me methyl
MeOH methanol
MS mass spectrometry
Ms methanesulfonyl (mesyl)
rt room temperature
RT retention time (HPLC)
singlet
t triplet
td triple doublet
TFA trifluoroacetic acid General Analytical Procedures The structure of representative compounds of this invention were confirmed using the following procedures.

Electron impact mass spectra (EI-MS) were obtained with a Hewlett Packard® 5989A mass spectrometer equipped with a Hewlett Packard® 5890 Gas Chromatograph with a J & W DB-5 column (0.25 uM coating; 30 m×0.25 mm). The ion source is maintained at 250° C. and spectra were scanned from 50-800 amu at 2 sec per scan.

High pressure liquid chromatography-electrospray mass spectra (LC-MS) were obtained using either a:

(A) Hewlett-Packard® 1100 HPLC equipped with a quaternary pump, a variable wavelength detector set at 254 nm, a YMC pro C-18 column (2×23 mm, 120 A), and a Finnigan® LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flow rate of 1.0 mL/min is used with an initial hold of 0.5 minutes and a final hold at 95% B of 0.5 minutes. Total run time is 6.5 minutes.

or (B) Gilson® HPLC system equipped with two Gilson 306 pumps, a Gilson 215 Autosampler, a Gilson® diode array detector, a YMC Pro C-18 column (2×23 min, 120 A), and a Micromass LCZ single quadrupole mass spectrometer with z-spray electrospray ionization. Spectra were scanned from 120-800 amu over 1.5 seconds. ELSD (Evaporative Light Scattering Detector) data is also acquired as an analog channel. The eluents were A: 2% acetonitrile in water with 0.02% TFA and B: 2% water in acetonitrile with 0.018% TFA. Gradient elution from 10% B to 90% over 3.5 minutes at a flowrate of 1.5 mL/min is used with an initial hold of 0.5 minutes and a final hold at 90% B of 0.5 minutes. Total run time is 4.8 minutes. An extra switching valve is used for column switching and regeneration.

Routine one-dimensional $^1$H NMR spectroscopy is performed on 300 MHz Varian® Mercury-plus spectrometers. The samples were dissolved in deuterated solvents obtained from Cambridge Isotope Labs®, and transferred to 5 mm ID Wilmad® NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$-$d_3$, 3.30 ppm for $CD_3OD$-$d_4$, 5.32 ppm for $CD_2Cl_2$-$d_4$ and 7.26 ppm for $CDCl_3$-d for $^1$H spectra.

Example 1

Preparation of 2-[6-(3-Chloro-4-fluoro-phenylamino)-10-thia-2,3,7,9-tetraazacyclopenta[a]fluoren-2-yl]-ethanol

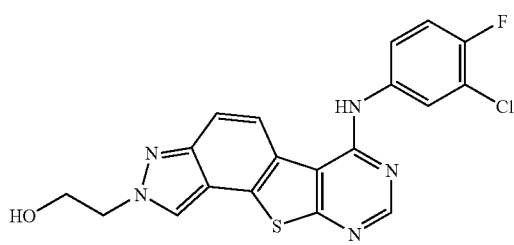

Step 1. Preparation of Ethyl 2-amino-4,7-dihydro-5H-spiro[1-benzothiophene-6,2'-[1,3]dioxolane]-3-carboxylate

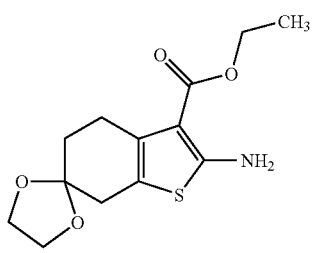

To 600 mL ethanol were sequentially 1,4-dioxa-spiro[4.5]decan-8-one (25.0 g, 0.160 mol), ethyl cyanoacetate (18.1 g, 0.160 mol), morpholine (14.0 g, 0.160 mol), and sulfur (5.5 g, 0.160 mol). The heterogeneous contents were stirred at room temperature for 4 days, after which time all the sulfur had dissolved. The homogeneous contents were concentrated under reduced pressure, and the residue diluted with EtOAc (200 mL). The mixture was washed with water (200 mL), and the layers were separated. The organic layer was dried over $MgSO_4$, filtered, and concentrated under reduced pressure to afford the desired product as a dark colored oil (45.0 g, 99%). $^1$H-NMR (DMSO-$d_6$) δ 7.20 (s, 2H), 4.10 (q, 2H), 3.87 (s, 4H), 2.66 (t, 2H), 2.59 (s, 2H), 1.71 (t, 2H), 1.18 (t, 3H); LCMS RT=2.58 min; [M+H]$^+$=284.2.

Step 2. Preparation of 3,5,6,8-tetrahydro-4H-spiro[1-benzothieno[2,3-d]pyrimidine-7,2'-[1,3]dioxolan]-4-one

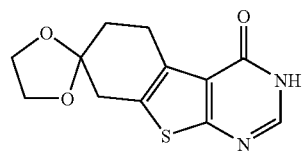

To a stirring solution of ethyl 2-amino-4,7-dihydro-5H-spiro[1-benzothiophene-6,2'-[1,3]dioxolane]-3-carboxylate (40.0 g, 0.142 mol) in formamide (225 mL) was added ammonium formate (17.8 g, 0.282 mol). The resulting mixture was stirred with at 140° C. for 16 h, after which time the heterogeneous contents were removed from heating, and allowed to cool to rt. The contents were filtered, the solid filter cake was washed with water (2×60 mL), and suction dried overnight to afford the desired product as an off-white solid (33.0 g, 88%). $^1$H-NMR (DMSO-$d_6$) δ 12.35 (broad s, 1H), 8.00 (s, 1H), 3.92 (s, 4H), 2.95 (t, 2H), 2.91 (s, 2H), 1.83 (t, 2H); LCMS RT=1.87 min; [M+H]$^+$=265.2.

Step 3. Preparation of 4-chloro-5,8-dihydro-6H-spiro[1-benzothieno[2,3-d]pyrimidine-7,2'-[1,3]dioxolane]

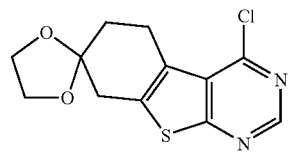

To a stirring solution of 3,5,6,8-tetrahydro-4H-spiro[1-benzothieno[2,3-d]pyrimidine-7,2'-[1,3]dioxolan]-4-one (20.0 g, 0.076 mol) in $POCl_3$ (200 mL) at 0° C. was added triethylamine (200 mL) over a 15 min period. The resulting mixtures were allowed to warm to rt, and then heated to 80° C. After 3 h, the contents were removed from heating, and allowed to cool to rt. The heterogeneous mixture was concentrated under reduced pressure. The residue was diluted with EtOAc (100 mL), and concentrated again to further remove the volatile materials. The residue was then diluted with EtOAc (100 mL) and the heterogeneous mixture poured onto a stirring mixture of ice-water/aq $NaHCO_3$ (800 mL). After 5 min stirring, the contents (pH≈7) were filtered and the solid filter cake washed with water. The product was dried in vacuum oven overnight to afford the desired product (20.7 g, 97%) as an off-white solid. $^1$H-NMR (DMSO-$d_6$) δ 8.82 (s, 1H), 3.97 (s, 4H), 3.10 (t, 2H), 3.07 (s, 2H), 1.95 (t, 2H); LCMS RT=2.45 min; [M+H]$^+$=283.1.

Step 4. Preparation of N-(3-chloro-4-fluorophenyl)-5,8-dihydro-6H-spiro[1-benzothieno[2,3-d]pyrimidine-7,2'-[1,3]dioxolan]-4-amine,

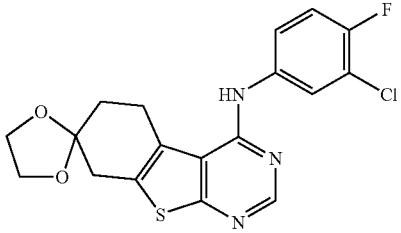

To a stirring solution of 4-chloro-5,8-dihydro-6H-spiro[1-benzothieno[2,3-d]pyrimidine-7,2'-[1,3]dioxolane] (7.0 g, 24.8 mmol) in ethanol (100 mL) was added 4-fluoro-3-chloroaniline (3.6 g, 24.8 mmol) and HCl (4N in dioxane, 0.05 mL). The contents were heated to reflux for 5 h, after which time the contents were removed from heating and allowed to cool to rt. The solvent was removed under reduced pressure, the crude residue suspended in aq NaHCO$_3$ (100 mL), and stirred for 15 min. The contents were again filtered, and the solid filter cake washed with water. The collected yellow solid was triturated with diethyl ether (50 mL) to afford the final product (5.5 g, 57%) as a light yellow solid. $^1$H-NMR (DMSO-d$_6$) δ 8.41 (s, 1H), 8.28 (s, 1H), 7.78 (dd, 1H), 7.58 (m, 1H), 7.35 (t, 1H), 3.97 (s, 4H), 3.22 (t, 2H), 3.00 (s, 2H), 1.93 (t, 2H); LCMS RT=3.26 min; [M+H]$^+$=392.3.

Step 5. Preparation of 4-(3-Chloro-4-fluoro-phenylamino)-5,8-dihydro-6H-benzo[4,5]thieno[2,3-d]pyrimidin-7-one

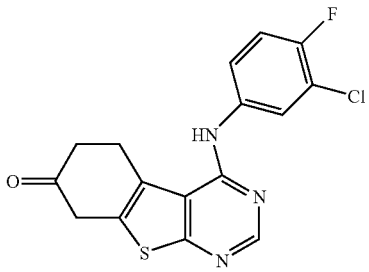

To a stirring acetic acid/water solution (4:1, 300 mL) was added N-(3-chloro-4-fluorophenyl)-5,8-dihydro-6H-spiro[1-benzothieno[2,3-d]pyrimidine-7,2'-[1,3]dioxolan]-4-amine (5.5 g, 14 mmol), and the contents heated at 80° C. for 12 h. The dark colored mixture was cooled to rt, and the solvent was removed under reduced pressure. The crude residue was suspended in aq NaHCO$_3$ (1N, 100 mL), stirred for 10 min, and filtered. The filtered solid was triturated with diethyl ether (100 mL) to afford the desired product (4.8 g, 98%) as a dark yellow solid. $^1$H-NMR (DMSO-d$_6$) δ 8.53 (s, 1H), 8.46 (s, 1H), 7.87 (dd, 1H), 7.60 (m, 1H), 7.40 (t, 1H), 3.73 (s, 2H), 3.43 (t, 2H), 2.64 (s, 2H); LCMS RT=3.01 min; [M+H]$^+$=348.2.

Step 6. Preparation of 4-(3-Chloro-4-fluoro-phenylamino)-8-dimethylaminomethylene-5,8-dihydro-6H-benzo[4,5]thieno[2,3-d]pyrimidin-7-one

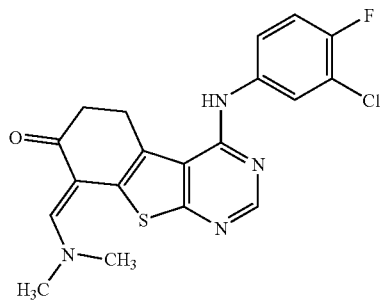

A slurry of 4-(3-chloro-4-fluoro-phenylamino)-5,8-dihydro-6H-benzo[4,5]thieno[2,3-d]pyrimidin-7-one (8.0 g, 0.023 mol) in toluene (80 mL) was prepared and N,N-dimethylformamide dimethyl acetal (3.2 mL, 0.024 mol) was added. The orange slurry turned dark purple upon heating in an oil bath at 80° C. After 1 h the solvent was evaporated in vacuo to yield a medium brown solid that was carried on directly to the next step. LCMS RT=3.06 min; [M+H]$^+$=403.2.

Step 7. Preparation of 2-{6-[(3-chloro-4-fluorophenyl)amino]-4,5-dihydro-2H-pyrimido[5',4':4,5]thieno[2,3-e]indazol-2-yl}ethanol

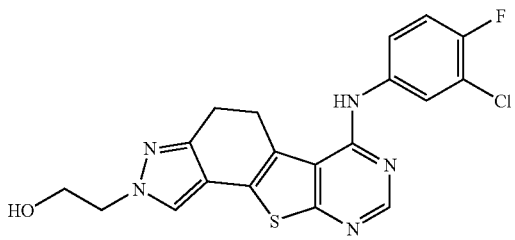

To a stirred solution of 4-(3-chloro-4-fluoro-phenylamino)-8-dimethylaminomethylene-5,8-dihydro-6H-benzo[4,5]thieno[2,3-d]pyrimidin-7-one (0.023 mol) in ethanol (93 mL) was added hydroxyethyl hydrazine (2.14 g, 0.024 mol). The slurry was heated in an oil bath at 50° C. for 3 h and then allowed to cool to room temperature overnight. The reaction mixture was filtered and the resulting solid was dried by vacuum filtration on a Buchner funnel for 2 h to yield an orange powdery solid (7.68 g, 80%). $^1$H NMR indicates a mixture of regioisomers (3:2 in favor of example 1). The above batch (7.2 g) of alcohol was combined with another batch (3.0 g, 3:1 regioisomer ratio in favor of example 1) and heated to near homogeneity in methoxybenzene (250 mL) at reflux. The mixture was cooled to 80° C. and EtOH (100 mL) was added while maintaining the internal temperature at about 80° C. The mixture was allowed to cool to room temperature with stirring. An orange solid precipitated and was collected by vacuum filtration (8.5 g, 7:3 regioisomer ratio in favor of example 1). The collected solid was transferred into a flask, reheated to reflux with methoxybenzene (300 mL), cooled to about 80° C., and diluted with EtOH (150 mL). The mixture was allowed to cool to room temperature overnight.

The orange solid was collected by vacuum filtration (3.8 g, 93% regioisomeric purity by LC). $^1$H NMR (DMSO-$d_6$) δ 8.58 (s, 1H), 8.39 (s, 1H), 7.94 (s, 1H), 7.88 (m, 1H), 7.61 (m, 1H), 7.40 (t, 1H), 4.93 (t, 1H), 4.11 (t, 2H), 3.75 (dt, 2H), 3.39 (t, 2H), 2.94 (t, 2H); LCMS RT=2.78 min; [M+H]$^+$=416.4.

Step 8. Preparation of 2-[6-(3-Chloro-4-fluoro-phenylamino)-10-thia-2,3,7,9-tetraazacyclopenta[a]fluoren-2-yl]-ethanol

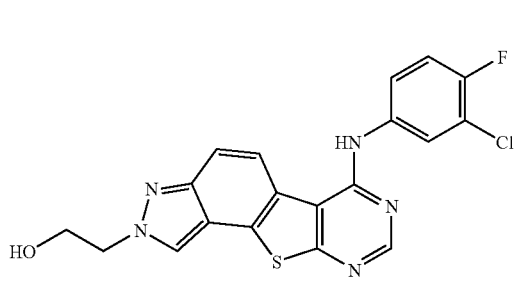

To a stirring solution of 2-{6-[(3-chloro-4-fluorophenyl)amino]-4,5-dihydro-2H-pyrimido[5',4':4,5]thieno[2,3-e]indazol-2-yl}ethanol (2.6 g, 6.25 mmol) in dioxane (25 mL) was added 2,3-dichloro-5,6-dicyanobenzoquinone (2.1 g, 9.38 mmol). The reaction mixture was heated to 90° C. for 2.5 h. The solid was filtered and separated by column chromatograph (90% methylene chloride/10% methanol) to give 2-[6-(3-chloro-4-fluoro-phenylamino)-10-thia-2,3,7,9-tetraazacyclopenta[a]fluoren-2-yl]-ethanol as a brown solid (3.0 g, yield 116% containing some carried over silica gel). $^1$H-NMR (DMSO-$d_6$) δ 9.25 (bs, 1H), 8.80 (s, 1H), 8.60 (s, 1H), 8.40 (t, 1H), 7.90 (d, 1H), 7.80 (d, 1H), 7.60 (m, 1H), 7.40 (t, 1H), 4.50 (t, 2H), 3.90 (t, 2H); LCMS RT=2.95 min; [M+H]$^+$=414.2.

Example 2

Preparation of Methanesulfonic Acid 2-[6-(3-chloro-4-fluoro-phenylamino)-10-thia-2,3,7,9-tetraaza-cyclopenta[a]fluoren-2-yl] ethyl ester

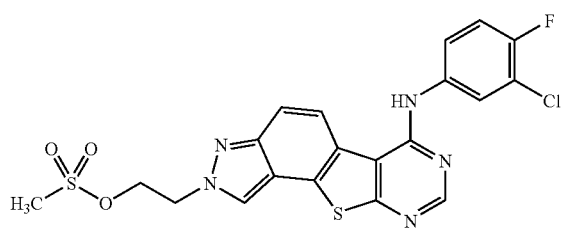

To a stirring solution of 2-[6-(3-chloro-4-fluoro-phenylamino)-10-thia-2,3,7,9-tetraazacyclopenta[a]fluoren-2-yl]-ethanol (2.53 g, 6.11 mmol) in acetonitrile (60 mL) was added methane sulfonic anhydride (2.1 g, 12.23 mmol) and pyridine (0.965 g, 12.23 mmol). It was stirred at room temperature for 2 h. The solid was filtered and further triturated with diethyl ether, oven dried overnight to give methanesulfonic acid 2-[6-(3-chloro-4-fluoro-phenylamino)-10-thia-2,3,7,9-tetraaza-cyclopenta[a]fluoren-2-yl]-ethyl ester as brown solid (2.0 g, 66.5%). $^1$H-NMR (DMSO-$d_6$) δ 9.30 (bs, 1H), 8.90 (s, 1H), 8.80 (t, 1H), 8.40 (d, 1H), 7.90 (m, 1H), 7.80 (d, 1H), 7.60 (m, 1H), 7.40 (t, 1H), 5.00 (t, 2H), 3.90 (t, 2H), 3.80 (s, 3H); LCMS RT=3.29 min; [M+H]$^+$=492.1.

Example 3

Preparation of (3-Chloro-4-fluoro-phenyl)-{2-[2-(2-methanesulfonyl-ethylamino)-ethyl]-2H-10-thia-2,3,79-tetraaza-cyclopenta[a]fluoren-6-yl}-amine

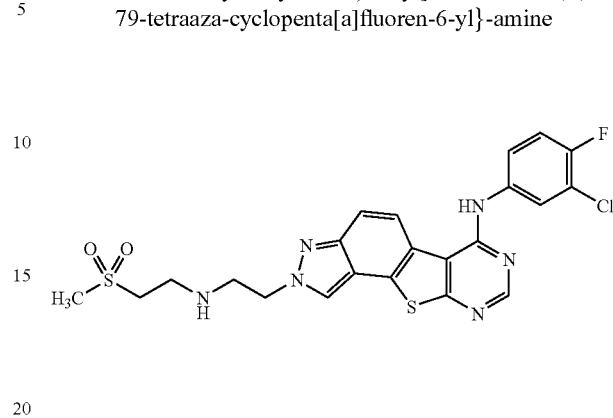

To a stirring solution of methanesulfonic acid 2-[6-(3-chloro-4-fluoro-phenylamino)-10-thia-2,3,7,9-tetraaza-cyclopenta[a]fluoren-2-yl]-ethyl ester (190 mg, 0.39 mmol) in DMF (3 mL) was added diisopropylethylamine (99 mg, 0.77 mmol) and 2-aminoethylmethylsulfone (143 mg, 1.16 mmol). It was heated to 80° C. for overnight. The crude mixture was diluted with methanol (5 mL) and it was separated by prep HPLC. The prep HPLC fractions were collected and solvent was removed by vacuum. The solid was re-dissolved by ethyl acetate (15 mL) and water (10 mL), sat. sodium carbonate solution (3 mL) was added. The organic layer was separated and dried over sodium sulfate. Evaporation of the solvents gave (3-chloro-4-fluoro-phenyl)-{2-[2-(2-methanesulfonyl-ethylamino)-ethyl]-2H-10-thia-2,3,7,9-tetraaza-cyclopenta[a]fluoren-6-yl}-amine as a white solid (10.3 mg, 5.1%) $^1$H-NMR (DMSO-$d_6$) δ 9.25 (bs, 1H), 8.80 (d, 1H), 8.60 (d, 1H), 8.40 (t, 1H), 7.90 (d, 1H), 7.80 (d, 1H), 7.60 (t, 1H), 7.40 (t, 1H), 4.60 (t, 2H), 3.20 (t, 2H), 2.90 (s, 3H), 2.10 (t, 2H), 2.05 (t, 2H); LCMS RT=2.89 min; [M+H]$^+$= 519.2.

Example 21

Preparation of 2-[6-({3-chloro-4-[(3-fluorobenzyl)oxy]phenyl}amino)-3H-pyrimido[5',4':4,5]thieno[2,3-e]indazol-3-yl]ethanol

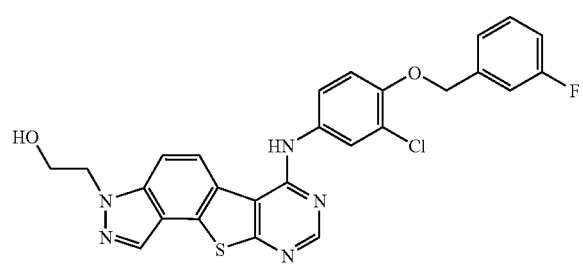

Step 1. Preparation of N-(3-Chloro-4-(3-fluoro-benzyloxy-phenylamine-5,8-dihydro-6H-spiro[1-benzothieno[2,3-d]pyrimidine-7,2'-[1,3]dioxolan]-4-amine

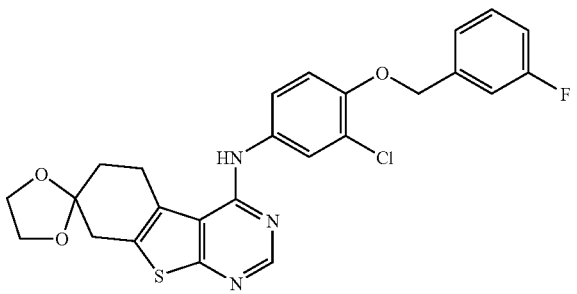

To 2-propanol (300 mL) were sequentially added 4-chloro-5,8-dihydro-6H-spiro[1-benzothieno[2,3-d]pyrimidine-7,2'-[1,3]dioxolane] (20.7 g, 73.2 mmol), 3-Chloro-4-(3-fluoro-benzyloxy)-phenylamine (18.4 g, 73.2 mmol), and HCl in dioxane (4N, 0.92 mL). The suspension was stirred with heating to 80° C., upon which the contents turn brown and homogeneous. After 15 h, the dark orange-yellow heterogeneous mixture was removed from heating, and allowed to cool to rt. The contents were filtered and the collected solid product dried under vacuum. The filtrate was concentrated under reduced pressure and the residue suspended in $CH_3OH$ (50 mL), upon which formation of a second crop of product ensues. The second crop was collected, and from this filtrate a third crop could also be obtained. The solid product crops were combined to afford the final product (33.5 g, 92%) as an off-white solid. $^1$H-NMR (DMSO-$d_6$) δ 1.90 (t, 2H), 3.00 (s, 2H), 3.26 (t, 2H), 3.97 (s, 4H), 5.22 (s, 2H), 7.11-7.30 (m, 4H), 7.41-7.55 (m, 2H), 7.74 (s, 1H), 8.33 (s, 1H), 8.39 (s, 1H); LCMS RT=3.63 min; [M+H]$^+$=498.3.

Step 2. Preparation of N-(3-Chloro-4-(3-fluoro-benzyloxy)-phenylamine)-5,8-dihydro-6H-benzo[4,5]thieno[2,3-d]pyrimidin-7-one

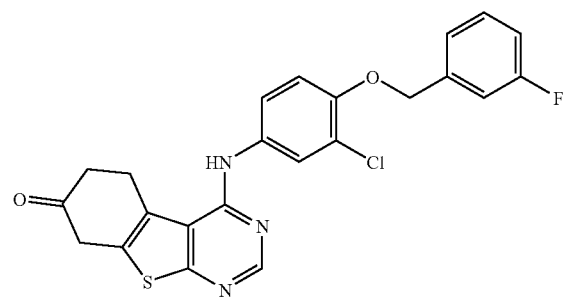

To a stirring acetic acid/$H_2O$ solution (4:1, 600 mL) was added N-(3-chloro-4-(3-fluoro-benzyloxy)-phenylamine)-5,8-dihydro-6H-spiro[1-benzothieno[2,3-d]pyrimidine-7,2'-[1,3]dioxolan]-4-amine (34.8 g, 69.8 mmol), and the contents heated at 80° C. for 16 h. The dark colored mixture was cooled to rt, and the solvent removed under reduced pressure. The crude residue was suspended in 1N NaHCO$_3$ aq solution (500 mL), stirred for 10 min, and filtered. The collected solid was again vigorously washed with $H_2O$ (500 mL) and filtered to afford the desired product, which was vacuum dried with heating at 40° C. for 24 h. The final product was collected (30.8 g, 97%) as an orange solid. $^1$H-NMR (DMSO-$d_6$) δ 2.66 (t, 2H), 3.44 (t, 2H), 3.74 (s, 2H), 5.23 (s, 2H), 7.14-7.32 (m, 4H), 7.40-7.52 (m, 2H), 7.75 (d, 1H), 8.34 (s, 1H), 8.39 (s, 1H); LCMS RT=3.50 min; [M+H]$^+$=454.1.

Step 3. Preparation of N-(3-Chloro-4-(3-fluoro-benzyloxy)-phenylamine)-8-dimethylaminomethylene-5,8-dihydro-6H-benzo[4,5]thieno[2,3-d]pyrimidin-7-one

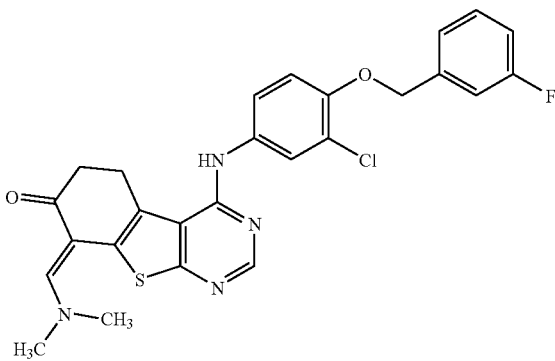

To 150 mL toluene were added N-(3-chloro-4-(3-fluoro-benzyloxy)-phenylamine)-5,8-dihydro-6H-benzo[4,5]thieno[2,3-d]pyrimidin-7-one (9.6 g, 18 mmol) and dimethylformamide-dimethylacetal (4.78 mL, 36 mmol). The contents were stirred at 70° C. for 4 h, after which time they were allowed to cool to rt. The heterogeneous mixture was filtered, collected solid washed with acetone (5 mL), and dried under hi-vac. The final product was collected (7.0 g, 70%) as a yellow solid. $^1$H-NMR (DMSO-$d_6$) (major rotamer) δ 2.53 (t, 2H), 3.10 (s, 6H), 3.24 (t, 2H), 5.21 (s, 2H), 7.10-7.21 (m, 3H), 7.26-7.33 (m, 2H), 7.40-7.50 (m, 2H), 7.75 (s, 1H), 8.15-8.40 (broad s, 1H), 8.30 (s, 1H); LCMS RT=3.75 min; [M+H]$^+$=509.2.

Step 4. Preparation of 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol

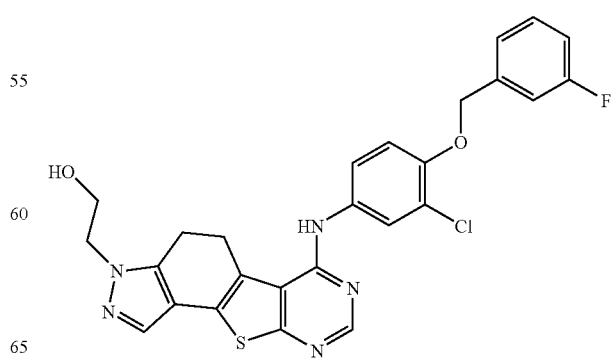

To 200 mL ethanol were added N-(3-chloro-4-(3-fluorobenzyloxy)-phenylamine)-8-dimethylaminomethylene-5,8-dihydro-6H-benzo[4,5]thieno[2,3-d]pyrimidin-7-one (12.0 g, 23.6 mmol), and then 2-tert-butyloxycarbonyl-2-hydroxyethylhydrazine (6.23 g, 35.4 mmol) as a 50 mL ethanol solution via dropping funnel over a 5 minute period. The reactants were stirred at reflux for 24 h, after which time they were removed from heating and allowed to cool to rt. The heterogeneous mixture was then cooled to 0° C. and a light tan solid was removed by filtration, dried under hi-vac to provide 9.8 g (65%) of solid. This solid was then dissolved in $CH_2Cl_2$ (100 mL) and cooled to 0° C. To the stirring suspension was added TFA (60 mL, 99%) via dropping funnel over a 15 minute period, during which time the contents become dark brown and homogeneous. The mixture was stirred with warming to rt over a 12 h period. The contents were concentrated to about 10% of its original volume, diluted with $CH_2Cl_2/H_2O$ (100 mL, 2:1), and stirred with cooling to 0° C. To the stirring mixture was added 175 mL aq 1N NaOH, to afford a pH=10 mixture which becomes heterogeneous on complete addition of base. The heterogeneous mixture was filtered and the filter cake washed with water. The collected solid was recrystallized from ethanol to furnish the final product (4.0 g, 67%, 44% for the two steps) as a light tan solid. $^1$H-NMR (DMSO-$d_6$) δ 3.02 (t, 2H), 3.33 (t, 2H), 3.66 (m, 2H), 4.12 (m, 2H), 4.87 (m, 1H), 5.24 (s, 2H), 7.10-7.30 (m, 4H), 7.40-7.53 (m, 2H), 7.61 (s, 1H), 7.73 (s, 11H), 8.31 (s, 11H), 8.38 (s, 11H); LCMS RT=3.30 min; $[M+H]^+$=522.1.

Step 5. Preparation of 2-[6-({3-chloro-4-[(3-fluorobenzyloxy]phenyl}amino)-3H-pyrimido[5',4':4,5]thieno[2,3-e]indazol-3-yl]ethanol

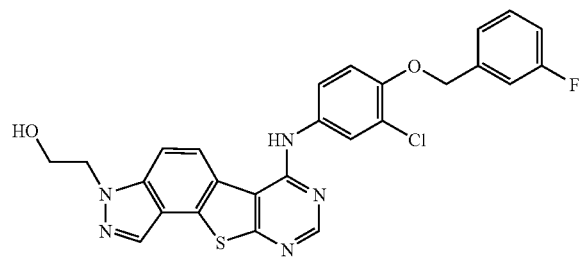

To a stirring solution of 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol (100 mg, 0.19 mmol) in dioxane (1 mL) was added 2,3-dichloro-5,6-dicyanobenzoquinone (65 mg, 0.29 mmol). The reaction mixture was heated to 90° C. for 2.5 h. The solid was filtered and separated by column chromatograph (90% methylene chloride/10% methanol) to give the desired product with some impurity (about 75% purity by LCMS). It was then recrystallized in methanol to give pure 2-[6-({3-chloro-4-[(3-fluorobenzyl)oxy]phenyl}amino)-3H-pyrimido[5',4':4,5]thieno[2,3-e]indazol-3-yl]ethanol as a brown solid (7.5 mg, yield 7.5%). $^1$H-NMR (DMSO-$d_6$) δ 9.10 (s, 1H), 8.50 (d, 2H), 8.45 (s, 1H), 7.90 (d, 1H), 7.80 (s, 1H), 7.50 (d, 1H), 7.45 (m, 1H), 7.35-7.20 (m, 4H), 5.25 (s, 2H), 4.90 (bs, 1H), 4.60 (t, 2H), 3.80 (t, 2H); LCMS RT=3.45 min; $[M+H]^+$=520.2.

Preparation of Intermediates

Preparation of tert-butyl 1-(2-hydroxyethyl)hydrazinecarboxylate

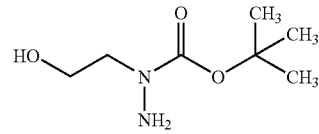

The title compound was prepared according to the literature (Krapcho, A. P. *J. Heterocyclic Chem.* 2000, 37, 47. $^1$H-NMR (CDCl$_3$) δ 3.81 (t, 2H), 3.73 (br, 3H), 3.57 (t, 2H), 1.48 (s, 9H); LCMS RT=1.74 min @ 100% aqueous; $[M+H]^+$= 176.9.

Preparation of 2-tert-butyldimethylsilyloxy-1-tert-butyloxycarbonyl-ethylhydrazine

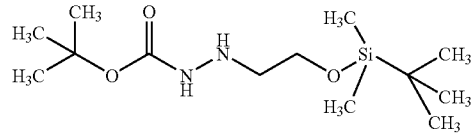

To 300 mL toluene were added (tert-butyldimethylsilyloxy)acetaldehyde (9.6 g, 49.6 mmol) and tert-butylcarbazate (6.75 g, 49.6 mmol). The mixture was stirred at 65° C. for 12 h, after which time the contents were removed from heating and allowed to cool to rt. The solvent was removed under reduced pressure to afford a colorless viscous oil (14.2 g, 97%). This oil was dissolved in ethanol (220 mL), the solution transferred to a 1 L Parr vessel, and 2.84 g Pd/C (10%) were added. The mixture was hydrogenated in a Parr shaker at 50 psi of $H_2$ atmosphere for 15 h. The contents were filtered through a thin pad of Celite® to remove the catalyst, and the filtrate concentrated in vacuo to afford the final product (14 g, 98%) as a white solid. $^1$H-NMR (CD$_2$Cl$_2$) δ 0.06 (s, 6H), 0.90 (s, 9H), 1.43 (s, 9H), 2.90 (t, 2H), 3.69 (t, 2H), 4.16 (br, 1H), 6.34 (br, 1H); LCMS RT=3.11 min; $[M+H]^+$=290.8.

Preparation of 3-Chloro-4-(3-fluoro-benzyloxy)-phenylamine

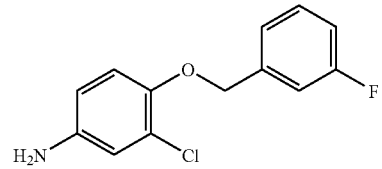

To 90 mL $CH_3CN$ was added 2-chloro-4-nitrophenol (15 g, 86.4 mmol) followed by potassium carbonate (17.9 g, 129.6 mmol). To the stirring suspension was added via dropping funnel a 10 mL $CH_3CN$ solution of 3-fluoro-benzylbromide (16.3 g, 86.4 mmol). The contents were stirred and heated at 70° C. for 18 h, after which time the bright yellow mixture was allowed to cool to rt. The yellow contents were poured onto H$_2$0 (200 mL) and stirred, upon which solid formation occurs. The solid was filtered and filter cake washed with additional H$_2$0 (50 mL). The collected solid was dried in vacuo, yielding 2-chloro-1-(3-fluoro-benzoyloxy)-4-nitro-benzene (23 g, 94%) as a white solid.

2-Chloro-1-(3-fluoro-benzoyloxy)-4-nitro-benzene (10 g, 35.5 mmol) was suspended in 50 mL acetic acid and 150 mL EtOAc in a 500 mL flask. Iron (9.9 g (177.5 mmol) was added to this suspension, and the mixture stirred at rt overnight. The reaction mixture was filtered through a thin pad of Celite®. The filtrate was concentrated in vacuo and neutralized with saturated Na$_2$CO$_3$ aq solution, followed by EtOAc extraction. The organic layer was washed with brine, dried over Na$_2$SO$_4$, and concentrated in vacuo. The resulting crude material was purified by flash chromatography eluting with 15% EtOAc/hexanes yielding 3-chloro-4-(3-fluoro-benzyloxy)-phenylamine as a brown solid [8.5 g, 95%, TLC R$_f$=0.4, 30% EtOAc/HEX.(3:7)]. $^1$H-NMR (DMSO-d$_6$) δ 4.94 (s, 2H), 5.00 (s, 2H), 6.40 (dd, 1H), 6.60 (s, 1H), 6.87 (d, 1H), 7.10-7.18 (m, 1H), 7.20-7.28 (m, 2H), 7.37-7.44 (m, 1H).

Preparation of
3-Chloro-4-(pyridin-2-ylmethoxy)-phenylamine

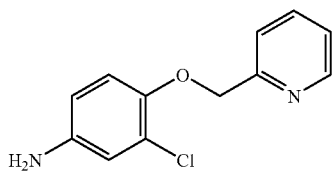

2-Chloro-4-nitro phenol 10 g (57.6 mmol, 1 eq), 2-(chloromethyl)pyridine hydrogen chloride 9.45 g (57.6 mmol, 1 equiv), cesium carbonate (41.3 g, 126.8 mmol, 2.2 equiv) and sodium iodide 8.64 g (57.6 mmol, 1 equiv) were suspended in 200 mL acetonitrile. The reaction mixture was stirred at 60° C. for 5 h. The resulted suspension was filtered and washed with 400 mL water, yielding 2-(2-chloro-4-nitro-phenoxymethyl)-pyridine (8 g, 52%) as a red solid.

2-(2-Chloro-4-nitro-phenoxymethyl)-pyridine (8 g, 30.2 mmol, 1 equiv) and 8.44 g iron (151.1 mmol, 5 equiv) in 100 mL acetic acid and 50 mL EtOAc were stirred at rt overnight. The reaction mixture was filtered through a pad of Celite®. The filtrate was concentrated in vacuo and neutralized with saturated Na$_2$CO$_3$ solution. The solution was extracted with EtOAc and the organic layer was washed with brine and concentrated in vacuo. The resulting crude material was purified by flash chromatography eluting with EtOAc/hexane (3:7) to give 3-chloro-4-(pyridin-2-ylmethoxy)-phenylamine (3.2 g, 52%) as a white solid. $^1$H-NMR (CDCl$_3$) δ 5.18 (s, 2H), 6.50 (dd, 1H), 6.76 (d, 1H), 6.80 (d, 1H), 7.22 (m, 1H), 7.64 (d, 1H), 7.73 (td, 1H), 8.55 (m, 1H); LCMS RT=0.89 min; [M+H]$^+$=235.1.

By using the methods described above, or methods analogous thereto, and by substituting the appropriate starting materials, other examples of the invention were prepared. Examples are summarized in Table 1 below.

TABLE 1

| Ex. No. | Structure | LCMS RT (min) | LCMS Ion [M + H]+ | IUPAC Name |
|---|---|---|---|---|
| 1 | 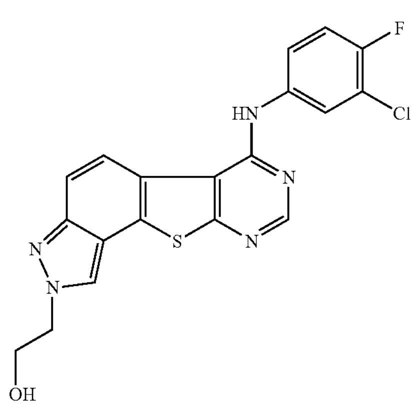 | 2.95 | 414.2 | 2-{6-[(3-chloro-4 fluorophenyl)amino]-2H-pyrimido[5',4':4,5]thieno[2,3-e]indazol-2-yl}ethanol |

TABLE 1-continued

| Ex. No. | Structure | LCMS RT (min) | LCMS Ion [M + H]+ | IUPAC Name |
|---|---|---|---|---|
| 2 | 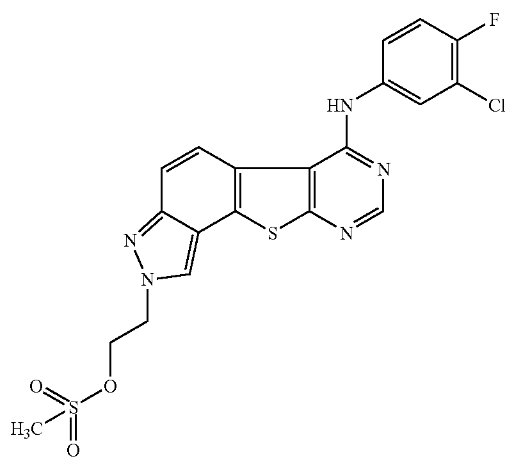 | 3.29 | 492.1 | 2-{6-[(3-chloro-4 fluorophenyl)amino]-2H-pyrimido[5',4':4,5]thieno[2,3-e]indazol-2-yl}ethyl methanesulfonate |
| 3 | 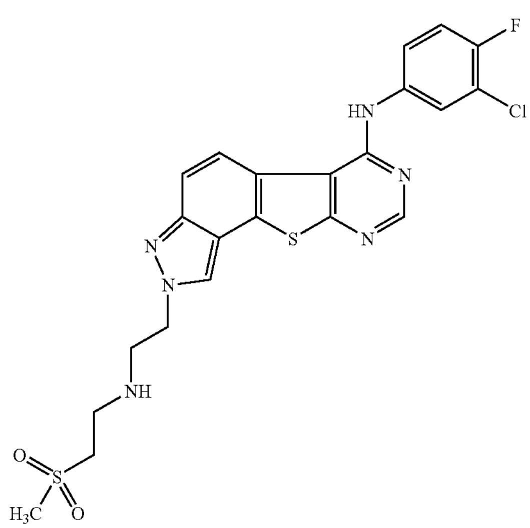 | 2.89 | 519.2 | N-(3-chloro-4-fluorophenyl)-2-(2-{[2-(methylsulfonyl)ethyl]amino}ethyl)-2H-pyrimido[5',4':4,5]thieno[2,3-e]indazol-6-amine |
| 4 | 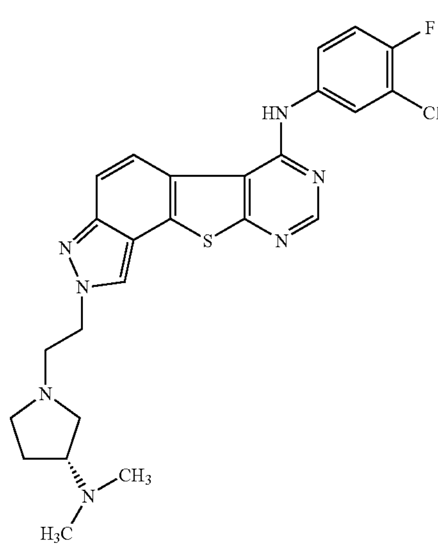 | 2.67 | 510.3 | N-(3-chloro-4-fluorophenyl)-2-(2-{2-[(3R)-3-(dimethylamino)pyrrolidin-1-yl]ethyl}-2H-pyrimido[5',4':4,5]thieno[2,3-e]indazol-6-amine |

TABLE 1-continued
| Ex. No. | Structure | LCMS RT (min) | LCMS Ion [M + H]+ | IUPAC Name |
|---|---|---|---|---|
| 5 | 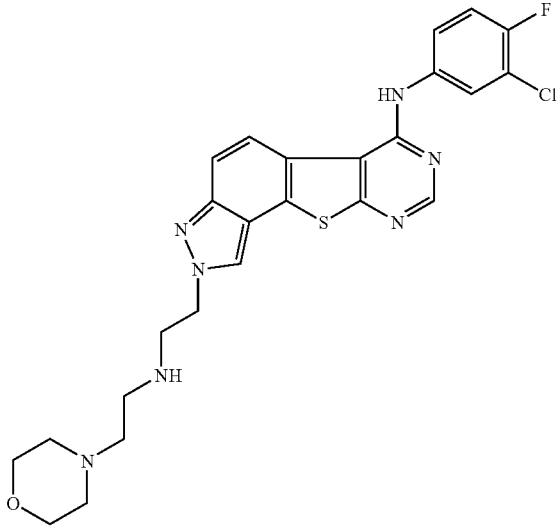 | 2.23 | 526.3 | N-(3-chloro-4-fluorophenyl)-2-{2-[(2-morpholin-4-ylethyl)amino]ethyl}-2H-pyrimido[5',4':4,5]thieno[2,3-e]indazol-6-amine |
| 6 | 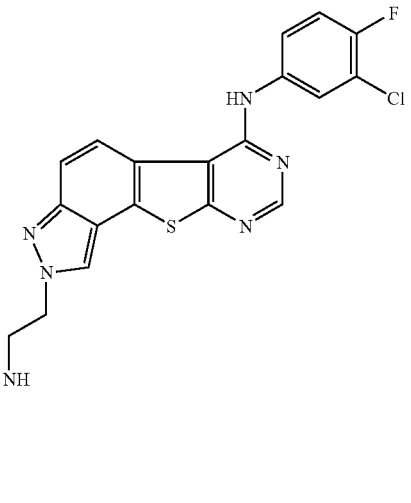 | 2.91 | 499.2 | N-(3-chloro-4-fluorophenyl)-2-{2-[(2-methoxyethyl)amino]ethyl}-2H-pyrimido[5',4':4,5]thieno[2,3-e]indazol-6-amine |
| 7 | 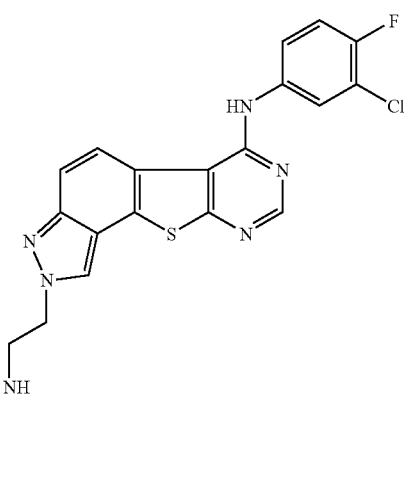 | 2.43 | 457.1 | 2-[(2-{6-[(3-chloro-4-fluorophenyl)amino]-2H-pyrimido[5',4':4,5]thieno[2,3-e]indazol-2-yl}ethyl)amino]ethanol |

TABLE 1-continued

| Ex. No. | Structure | LCMS RT (min) | LCMS Ion [M + H]+ | IUPAC Name |
|---|---|---|---|---|
| 8 | 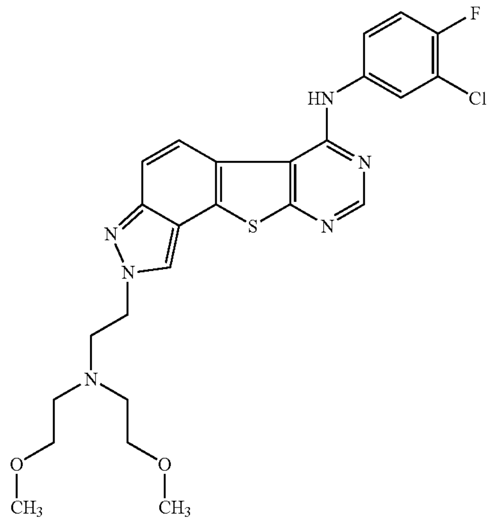 | 2.66 | 529.1 | 2-{2-[bis(2-methoxyethyl)amino]ethyl}-N-(3-chloro-4-fluorophenyl)-2H-pyrimido[5',4':4,5]thieno[2,3-e]indazol-6-amine |
| 9 | 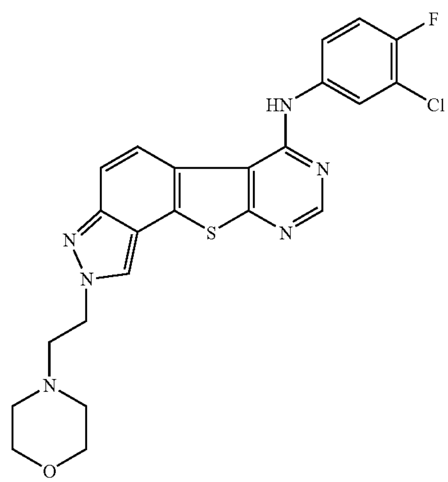 | 2.49 | 483.2 | N-(3-chloro-4-fluorophenyl)-2-(2-morpholin-4-ylethyl)-2H-pyrimido[5',4':4,5]thieno[2,3-e]indazol-6-amine |
| 10 | 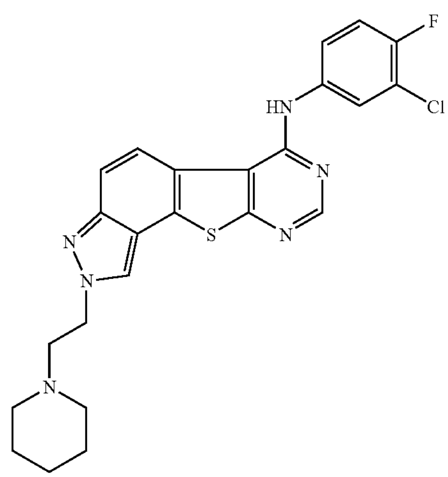 | 2.45 | 482.1 | N-(3-chloro-4-fluorophenyl)-2-(2-piperazin-1-ylethyl)-2H-pyrimido[5',4':4,5]thieno[2,3-e]indazol-6-amine |

TABLE 1-continued

| Ex. No. | Structure | LCMS RT (min) | LCMS Ion [M + H]+ | IUPAC Name |
|---|---|---|---|---|
| 11 | 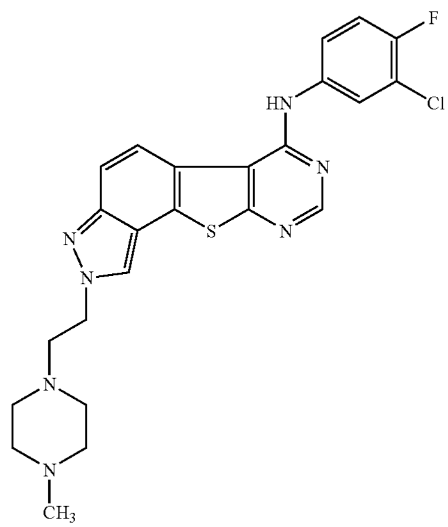 | 2.48 | 496.1 | N-(3-chloro-4-fluorophenyl)-2-[2-(4-methylpiperazin-1-yl)ethyl]-2H-pyrimido[5',4':4,5]thieno[2,3-e]indazol-6-amine |
| 12 | 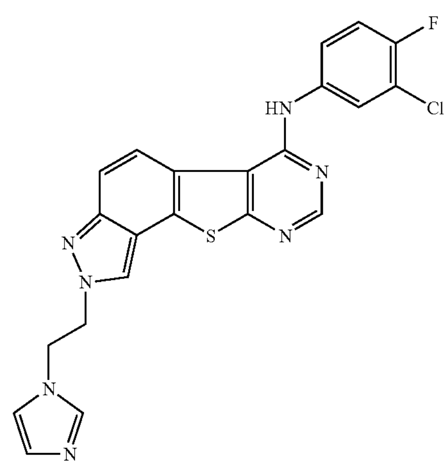 | 2.85 | 448.3 | N-(3-chloro-4-fluorophenyl)-2-[2-(1H-imidazol-1-yl)ethyl]-2H-pyrimido[5',4':4,5]thieno[2,3-e]indazol-6-amine |
| 13 | 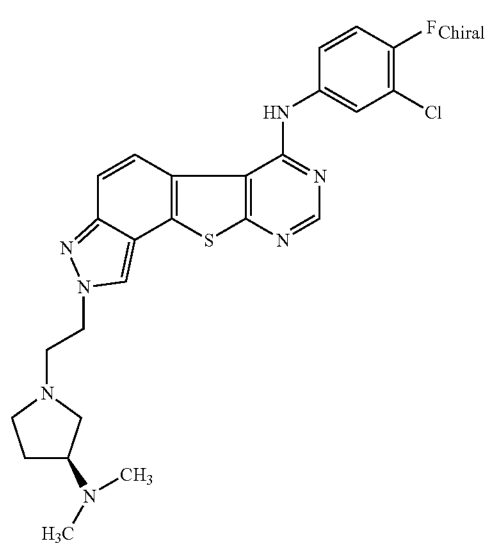 | 2.67 | 510.3 | N-(3-chloro-4-fluorophenyl)-2-{2-[(3S)-3-(dimethylamino)pyrrolidin-1-yl]ethyl}-2H-pyrimido[5',4':4,5]thieno[2,3-e]indazol-6-amine |

TABLE 1-continued
| Ex. No. | Structure | LCMS RT (min) | LCMS Ion [M + H]+ | IUPAC Name |
|---|---|---|---|---|
| 14 | 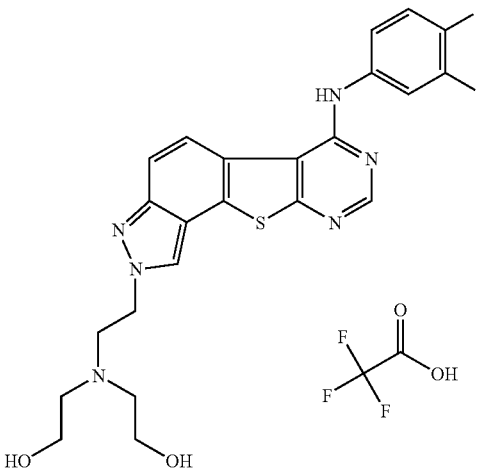 | 2.3 | 501.3 | 2,2'-[(2-{6-[(3-chloro-4-fluorophenyl)amino]-2H-pyrimido[5',4':4,5]thieno[2,3-e]indazol-2-yl}ethyl)imino]diethanol trifluoroacetate (salt) |
| 15 | 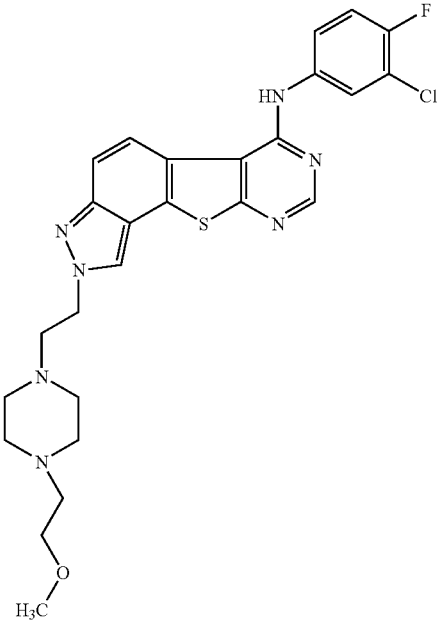 | 2.54 | 540.4 | N-(3-chloro-4-fluorophenyl)-2-{2-[4-(2-methoxyethyl)piperazin-1-yl]ethyl}-2H-pyrimido[5',4':4,5]thieno[2,3-e]indazol-6-amine |

TABLE 1-continued

| Ex. No. | Structure | LCMS RT (min) | LCMS Ion [M + H]+ | IUPAC Name |
|---|---|---|---|---|
| 16 | 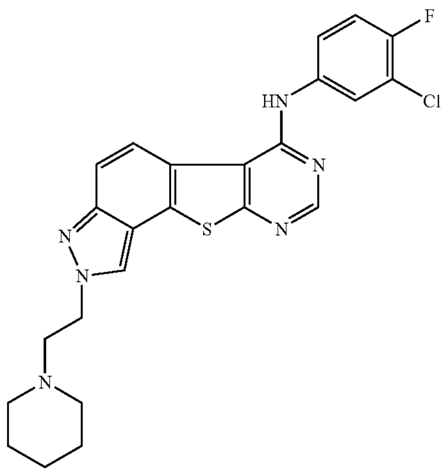 | 2.59 | 481.4 | N-(3-chloro-4-fluorophenyl)-2-(2-piperidin-1-ylethyl)-2H-pyrimido[5',4':4,5]thieno[2,3-e]indazol-6-amine |
| 17 | 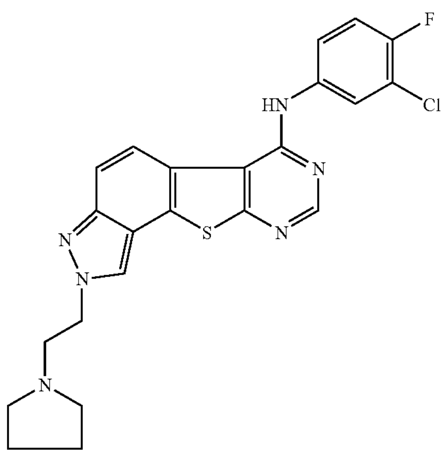 | 2.5 | 467.4 | N-(3-chloro-4-fluorophenyl)-2-(2-pyrrolidin-1-ylethyl)-2H-pyrimido[5',4':4,5]thieno[2,3-e]indazol-6-amine |
| 18 | 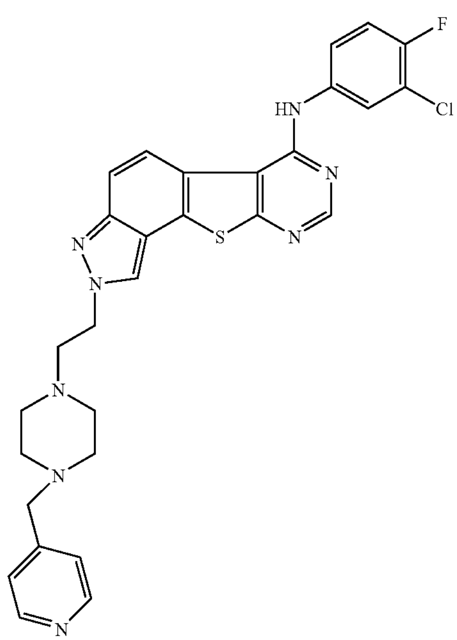 | 2.29 | 573.2 | N-(3-chloro-4-fluorophenyl)-2-{2-[4-(pyridin-4-ylmethyl)piperazin-1-yl]ethyl}-2H-pyrimido[5',4':4,5]thieno[2,3-e]indazol-6-amine |

TABLE 1-continued
| Ex. No. | Structure | LCMS RT (min) | LCMS Ion [M + H]+ | IUPAC Name |
|---|---|---|---|---|
| 19 | 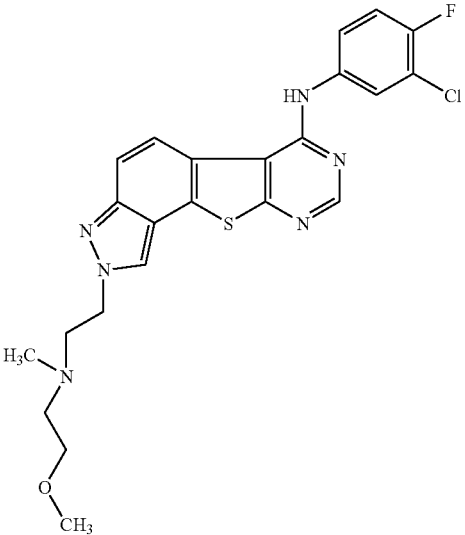 | 2.55 | 485.4 | N-(3-chloro-4-fluorophenyl)-2-{2-[(2-methoxyethyl)(methyl)amino]ethyl}-2H-pyrimido[5',4':4,5]thieno[2,3-e]indazol-6-amine |
| 20 | 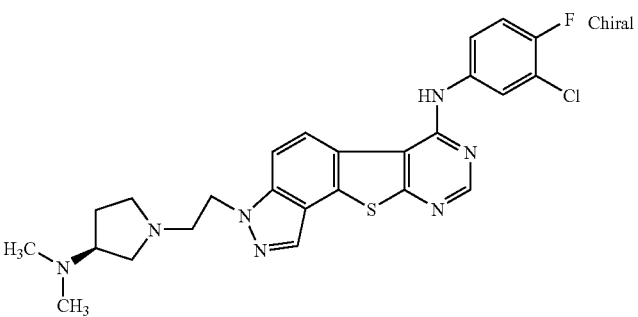 | 2.69 | 510.2 | N-(3-chloro-4-fluorophenyl)-3-{2-[(3S)-3-(dimethylamino)pyrrolidin-1-yl]ethyl}-3H-pyrimido[5',4':4,5]thieno[2,3-e]indazol-6-amine |
| 21 | 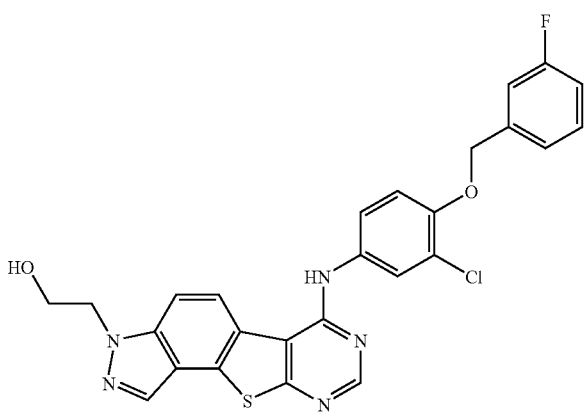 | 3.45 | 520.2 | 2-[6-({3-chloro-4-[(3-fluorobenzyl)oxy]phenyl}amino)-3H-pyrimido[5',4':4,5]thieno[2,3-e]indazol-3-yl]ethanol |

TABLE 1-continued

| Ex. No. | Structure | LCMS RT (min) | LCMS Ion [M + H]+ | IUPAC Name |
|---|---|---|---|---|
| 22 | 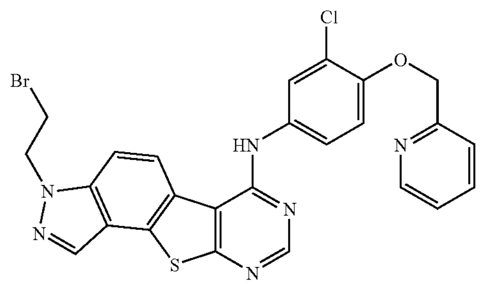 | 2.98 | 565 | 3-(2-bromoethyl)-N-[3-chloro-4-(pyridin-2-ylmethoxy)phenyl]-3H-pyrimido[5',4':4,5]thieno[2,3-e]indazol-6-amine |

B. EVALUATION OF PHYSIOLOGICAL ACTIVITY

The utility of the compounds of the present invention can be illustrated, for example, by their activity in vitro in the in vitro tyrosin kinase inhibition assay described below.

In Vitro Tyrosin Kinase Inhibition Assay

The ability of compounds in the present invention to inhibit the tyrosine kinase activities of EGFR (erbB1) and HER2 (erbB2) in cellular systems was measured using ELISA (Enzyme-Linked Immunosorbent Assay) shown below.

Inhibition of tyrosine phosphorylation of HER1 in A431 Cells Materials:
Essentially fatty acid free Bovine Albumin: SIGMA #A9205 30% solution
96-well tissue culture treated plate
96-well EIA/RIA plates: Corning Costar #9018
BSA for blocking Kirkegaard & Perry: #50-61-00
DPBS w/o calcium and magnesium: Gibco/Invitrogen #14190
Wash Buffer: TBS/0.05% Tween
RhEGF: Gibco/Invitrogen 313427-051
Her-1 Ab: Upstate Anti-EGF receptor (neutralizing) mouse monoclonal IgG clone
LA1 #05-101.
Biosource phospho-specific Anti-EFG receptor (pY1068): #44-788G
Amersham Biosciences ECL Anti-rabbit IgG peroxidase-linked antibody: #NA934
TMB Substrate:Sigma #T-8665

Lysis Buffer (Kept on Ice):
TBS
1% Triton X-100
1 mM EDTA
1 mM Sodium orthovanadate
10 mM Beta glycerol phosphate
1 mM Sodium Fluoride
10 µg/ml Aprotinin
IX Roche Complete EDTA-free protease inhibitor cocktail (1 tablet/2 mL $H_2O$=25x)

Method: Note: All antibody plate washes were performed with plate washer.
EGF was performed using a Zymark auto liquid handler unit.

Day 1
Plate 30K A431 cells/well in serum-containing media in 96-well plate.
Incubate at 37° C.
Antibody Plates Dilute Her-1 neutralizing antibody in PBS to a final concentration of 1 ug/mL.
Add 100 µL/well to 96-well EIA/RIA plates. Incubate overnight at 4° C. on rotator.

Day 2
BSA block antibody plates: Make stock of TBST containing 3% KPL BSA. Wash plates 3x200 µL/well with TBST. Add 100 µL/well TBST/3% BSA.
Incubate at 37° C. for at least one hour.
Make stock of basal media containing 0.1% BSA and sterile filter.
Wash plates 2x100 µL/well with basal media and add 100 µL/well basal media/0.1% BSA.
Incubate at 37° C. for 2 h.
Create master compound dilution plate at concentrations 3-fold final concentrations. Initial concentration is in 0.1% BSA/Media. Subsequent dilutions performed in 0.1% BSA/Media containing 0.3% DMSO to match that found in the initial drug concentration. Keep two columns without drug for drug free comparison These columns should contain media/0.1% BSA/DMSO only. Transfer 50 µL/well to cell plate containing 0.1% BSA/Media.
Incubate at 37° C. for 2 hrs.
EGF Stimulation: Make 500 ng/ml stock of rhEGF (10x) in 0.1% BSA/Media. Keeping one drug-free column unstimulated, add 15 µL/well to rest of cell plate (50 ng/ml final).
For each compound, add to entire series of drug concentration at same time to insure equal stimulation time for all concentrations for that compound. Incubate 5 min at r.t. with periodic swirling. Immediately place on ice 5 min.
Remove media and wash plate 2x150 uL/well with cold DPBS. Add 150 µL/well cold Lysis Buffer containing protease inhibitors. Incubate on ice 30 min rotating.
Antibody coated plates: wash plates 3x200 µL/well with TBST. Transfer 100 µL/well lysate to antibody coated plate. Incubate 4° C. overnight rotating.

Day 3
Wash plate 3x200 µL/well with TBST and add 100 µL/well EGFR phospho specific Ab diluted to Ab100 ng/ml diluted/ml TBS/3% BSA. Incubate on rotator r.t. 1 h.

Wash plate 3×200 μL/well with TBST and add 100 μL/well Anti-rabbit IgG Ab diluted 1:9000

Incubate on rotator at r.t. for 1 h.

Wash plate 3×200 μL/well with TBST and add 50 μL/well TMB substrate. Incubate r.t. till developed (blue, while maintaining dose response). Stop with 100 μL/well 1M HCL and read at 450 nm.

Inhibition of tyrosine phosphorylation of HER2 in BT474 Cells

Materials:
BT474 Cells grown in RPMI 1640 Gibco #11875-093, 10% FCS
Essentially fatty acid free Bovine: Albumin SIGMA #A9205 30% solution
96-well tissue culture treated plate
EIA/RIA 96-well plates: Corning, Inc #9018
HER2/ab-2: NeoMarkers, Inc. c-erbB-2/HER-2/neu Oncoprotein/Ab-2 (Clone 9G6.10) #MS-229-PABX
HER2/Ab-18: NeoMarkers, Inc. c-erbB-2/HER-2/neu biotin-tagged (Phospho-specific) Ab-18 (Clone PN2A): #MS-1072-BO
Amersham Pharmacia Biotech Streptavidin-Horseradish Peroxidase Conjugate: #RPN 1231
TMB Substrate: Sigma #T-8665
Wash Buffer: TBS/0.05% Tween
Lysis Buffer:
TBS
1% Triton X-100
1 mM EDTA
1 mM Sodium orthovanadate
10 mM Beta glycerol phosphate
1 mM Sodium Fluoride
10 ug/ml Aprotinin
1X Roche Complete EDTA-free protease inhibitor cocktail (1 tablet/2 mls H2O)

Method:

Day 1

Plate 30K BT474 cells/well (RPMI/10% FCS) in tissue culture treated 96-well dish columns 2-12.

Add 100 μL growth media to column one to act as signal to noise factor.

Incubate at 37° C.

Coat Antibody Plates: Dilute Her-2 Ab-2 in PBS to a final concentration of 2 μg/ml.

Add 100 μL/well to 96-well EIA/RIA plates. Incubate o.n. at 4 degrees C. on rotator.

Day 2

Block antibody plates: Wash plates 3×200 μL/well with TBST. Add 100 μL/well TBST/3% BSA.

Incubate 37° C. at least one hour.

Make stock of basal media containing 0.1% BSA and sterile filter.

Wash cell plates 2×100 μL/well with basal media and add 100 μL/well basal media/0.1% BSA.

Incubate 37° C. Incubate at 37° C. for 2 h.

Create master compound dilution plate at concentrations 3-fold desired final concentrations.

Initial concentration is in 0.1% BSA/Media. Subsequent dilutions performed in 0.1% BSA/Media containing 0.3% DMSO to match that found in the initial drug concentration. Keep two columns without drug for drug-free comparison These columns should contain media/0.1% BSA/DMSO only. Transfer 50 μL/well to cell plate containing 0.1% BSA/Media.

Incubate at 37° C. for 2 h.

Remove media and wash plate 2×150 μL/well with cold DPBS. Add 150 uL/well cold Lysis Buffer containing protease inhibitors. Incubate on ice 30 min rotating.

Wash blocked antibody coated plate 3×200 μL/well with TBST. Transfer 100 μL/well lysate to antibody coated plate. Incubate on rotator at 4° C. overnight.

Day 3

Wash plate 3×200 μL/well with TBST and add 100 μL/well Biotin-tagged phospho-Her-2 antibody diluted to 20 ng/mL in TBS/3% BSA. Incubate on rotator at r.t. for 1 h.

Wash plate 3×200 uL/well with TBST and add 100 uL/well Streptavidin-Horseradish Peroxidase Conjugate diluted to 100 ng/mL in TBS/3% BSA. Incubate on rotator at r.t. for 1 h.

Wash plate 3×200 μL/well with TBST and add 50 μL/well TMB substrate. Incubate r.t. till developed (blue, while maintaining dose response). Stop with 100 μL/well 1M HCL and read at 450 nm.

In Vitro Tumor Cell Proliferation Assay

The utility of the compounds of the present invention can be demonstrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays.

Many of the compounds and compositions described herein, exhibit anti-proliferative activity with $IC_{50} \leq 50$ μM in either of the following specified cell lines and are thus useful to prevent or treat the disorders associated with hyper-proliferation. The following assay is one of the methods by which compound activity relating to treatment of the disorders identified herein can be determined.

In Vitro Tumor Cell Proliferation Assay

The tumor cell proliferation assay used to test the compounds of the present invention involves a readout called Cell Titer-Glow® Luminescent Cell Viability Assay developed by Promega® (Cunningham, B A "A Growing Issue: Cell Proliferation Assays, Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

A431 cells (human epidermoid carcinoma, ATCC # HTB-20) and BT474 (human breast carcinoma, ATCC # CRL-1555) were plated at a density of $2.5 \times 10^3$ cells/well in 96 well black-clear bottom tissue culture plates in RPMI media with 10% Fetal Bovine Serum and incubated at 37° C. Twenty-four h later, test compounds are added at a final concentration range from as high 100 μm to as low 64 pM depend on the activities of the tested compounds in serial dilutions at a final DMSO concentration of 0.1%. Cells were incubated for 72 h at 37° C. in complete growth media after addition of the test compound. After 72 h of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR 2 using Luminescence protocol, and analyzed with Analyze5 software to generate $IC_{50}$ values. Representative compounds of this invention showed inhibition of tumor cell proliferation in this assay.

For determination of $IC_{50}$'s, a linear regression analysis can be used to determine drug concentration which results in a 50% inhibition of cell proliferation using this assay format. The anti-proliferative activities of selective sets of compounds are listed below. In A431 cells, Examples 1-7, 9-11, 14-18, and 20-21 have $IC_{50}$'s$\leqq$5 µM; whereas examples 8, 12, 13, 19, and 22 have $IC_{50}$'s$\leqq$50 µM. In BT474 cells, examples 1-7, 9-11, 13-18, and 20-22 have $IC_{50}$'s$\leqq$50 µM; whereas examples 8, 12, and 19 have $IC_{50}$'s$\leqq$50 µM.

C. OPERATIVE EXAMPLES RELATING TO PHARMACEUTICAL COMPOSITIONS

The compounds according to the invention can be converted into pharmaceutical preparations as follows:

Tablet:

Composition:

100 mg of the compound of EXAMPLE 1, 50 mg of lactose (monohydrate), 50 mg of maize starch (native), 10 mg of polyvinylpyrrolidone (PVP 25) (from BASF®, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Orally Administrable Suspension:

Composition:

1000 mg of the compound of Example 1, 1000 mg of ethanol (96%), 400 mg of Rhodigel (xanthan gum from FMC®, Pennsylvania, USA) and 99 g of water.

A single dose of 100 mg of the compound according to the invention is provided by 10 mL of oral suspension.

Preparation:

The Rhodigel is suspended in ethanol and the active component is added to the suspension. The water is added with stirring. Stirring is continued for about 6 h until the swelling of the Rhodigel is complete.

The invention claimed is:
1. A compound of formula

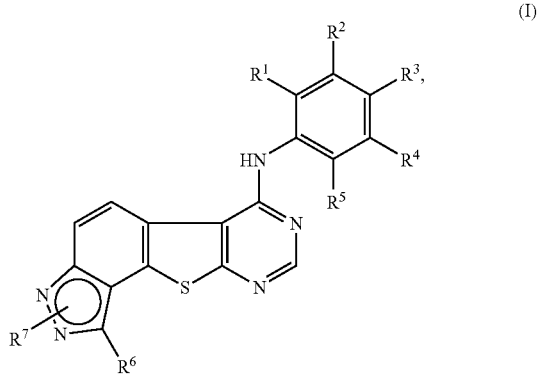

(I)

wherein
$R^1$ is selected from the group consisting of hydrogen, methyl, ethyl, and halo;
$R^2$ is selected from the group consisting of hydrogen, methyl, ethyl, and halo;
$R^3$ is selected from the group consisting of hydrogen, alkyl, halo, hydroxy, alkoxy, trifluoromethoxy, benzyloxy, halogenated benzyloxy, alkylated benzyloxy, pyridoxy, alkylated pyridoxy, halogenated pyridoxy, pyridylmethoxy, halogenated pyridylmethoxy, and N-morpholinyl, or
$R^2$ and $R^3$, together with the carbon atoms to which they are attached, form an pyrazole ring, wherein said pyrazole ring can optionally be substituted with 0, 1 or 2 substituents independently selected from the group consisting of alkyl, benzyl, halogenated benzyl, pyridylmethoxy, and halogenated pyridylmethoxy;
$R^4$ is selected from the group consisting of hydrogen, alkyl, cyano, and halo;
$R^5$ is selected from the group consisting of hydrogen, alkyl, and halo;
$R^6$ is selected from the group consisting of hydrogen, and alkyl;
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, hydroxy, alkoxy, alkylsulfonyloxy, and amino, or
$R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or $R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$, wherein $R^{7-2}$ is oxo, or wherein $R^{7-2}$ is alkylamino, wherein said alkylamino can optionally be substituted with 0, 1 or 2 substituents independently selected from the group consisting of oxo, hydroxy, alkoxy, amino, and alkylamino;

or a salt thereof.

2. The compound of claim 1, wherein $R^1$ is hydrogen;

$R^2$ is hydrogen;

$R^3$ is selected from the group consisting of hydrogen, halo, hydroxy, methoxy, ethoxy, n-propyloxy, i-propyloxy, trifluoromethoxy, benzyloxy, halogenated benzyloxy, pyridoxy, methylated pyridoxy, ethylated pyridoxy, halogenated pyridoxy, pyridylmethoxy, halogenated pyridylmethoxy, and N-morpholinyl, or $R^2$ and $R^3$, together with the carbon atoms to which they are attached, form an pyrazole ring, wherein said pyrazole ring can optionally be substituted with 0 or 1 substituents benzyl;

$R^4$ is selected from the group consisting of hydrogen, methyl, ethyl, n-propyl, i-propyl, cyano, and halo;

$R^5$ is hydrogen;

$R^6$ is hydrogen;

$R^7$ is selected from the group consisting of hydrogen, methyl, ethyl, n-propyl, i-propyl, n-butyl, i-butyl, t-butyl, and amino, or $R^7$ is alkyl selected from the group consisting of methyl, ethyl, and n-propyl, wherein said alkyl is substituted with 1 or 2 independently selected substituents $R^{7-1}$, wherein $R^{7-1}$ is selected from the group consisting of halo, hydroxy, methoxy, ethoxy, n-propyloxy, i-propyloxy, methylsulfonyloxy, amino, or $R^{7-1}$ is alkylamino, wherein said alkylamino can optionally be substituted with 0, 1 or 2 substituents independently selected from the group consisting of hydroxy, methoxy, ethoxy, n-propyloxy, i-propyloxy, amino, methylamino, ethylamino, dimethylamino, diethylamino, methylethylamino, methylsulfonyl, N-pyrrolidinyl, and N-morpholinyl, or $R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0 or 1 substituents independently selected from the group consisting of methyl, ethyl, n-propyl, i-propyl, halo, hydroxy, methoxy, ethoxy, n-propyloxy, i-propyloxy, amino, methylamino, ethylamino, dimethylamino, diethylamino, methylethylamino, hydroxymethyl, hydroxyethyl, methoxymethyl, methoxyethyl, carboxyl, methoxycarbonyl, ethoxycarbonyl, n-propyloxycarbonyl, i-propyloxycarbonyl, n-butyloxycarbonyl, i-butyloxycarbonyl, t-butyloxycarbonyl, N-pyrrolidinyl, N-piperidinyl, N-piperazinyl, pyrazinyl, benzyl, and pyridylmethyl;

or a salt thereof.

3. The compound of claim 1, wherein $R^1$, $R^2$, and $R^5$ are hydrogen, $R^3$ is 2-pyridylmethoxy and $R^4$ is chloro.

4. The compound of claim 1, wherein $R^1$, $R^2$, and $R^5$ are hydrogen, $R^3$ is fluoro and $R^4$ is chloro.

5. The compound of claim 1, wherein $R^1$, $R^2$, $R^4$, and $R^5$ are hydrogen, and $R^3$ is 3-fluorobenzyloxy.

6. A process for preparing the compounds of the formula (I), wherein a compound of formula (II)

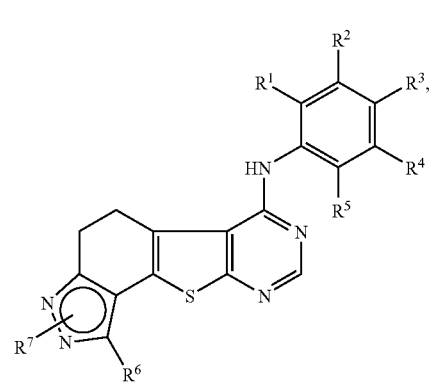

wherein $R^1$ to $R^7$ have the meaning indicated in claim 1, is oxidized with a oxidising agent or oxidant.

7. A pharmaceutical composition comprising a compound according to claim 1.

8. The pharmaceutical composition according to claim 7 in combination with at least one pharmaceutically acceptable excipient.

9. A process for preparing a pharmaceutical composition comprising a compound according to claim 1 in combination with at least one pharmaceutically acceptable excipient, comprising the steps of combining at least one compound of claim 1 with at least one pharmaceutically acceptable excipient, mixing the combination and bringing the combination into a suitable administration form.

10. The packaged pharmaceutical composition comprising a container comprising the pharmaceutical composition of claim 7 and instructions for using the pharmaceutical composition.

* * * * *